United States Patent
Amendola et al.

(10) Patent No.: US 12,012,613 B2
(45) Date of Patent: Jun. 18, 2024

(54) GENETICALLY ENGINEERED HEMATOPOIETIC STEM CELL AS A PLATFORM FOR SYSTEMIC PROTEIN EXPRESSION

(71) Applicants: GENETHON, Evry (FR); UNIVERSITE D'EVRY-VAL-D'ESSONE, Evry (FR); INSTITUT NATIONAL DE LA SANTE ET DE LA RECHERCHE MEDICALE (INSERM), Paris (FR)

(72) Inventors: Mario Amendola, Paris (FR); Giulia Pavani, Paris (FR)

(73) Assignees: Genethon, Paris (FR); Institut National De La Sante Et De La Recherche Medicale, Paris (FR)

( * ) Notice: Subject to any disclaimer, the term of this patent is extended or adjusted under 35 U.S.C. 154(b) by 515 days.

(21) Appl. No.: 16/961,483

(22) PCT Filed: Jan. 11, 2019

(86) PCT No.: PCT/EP2019/050710
§ 371 (c)(1),
(2) Date: Jul. 10, 2020

(87) PCT Pub. No.: WO2019/138082
PCT Pub. Date: Jul. 18, 2019

(65) Prior Publication Data
US 2020/0377857 A1 Dec. 3, 2020

(30) Foreign Application Priority Data
Jan. 12, 2018 (EP) ..................................... 18305026

(51) Int. Cl.
*C12N 5/0789* (2010.01)
*A61K 35/28* (2015.01)
*C12N 9/22* (2006.01)
*C12N 15/113* (2010.01)

(52) U.S. Cl.
CPC ............ *C12N 5/0647* (2013.01); *A61K 35/28* (2013.01); *C12N 9/22* (2013.01); *C12N 15/113* (2013.01); *C12N 2310/20* (2017.05); *C12N 2800/80* (2013.01)

(58) Field of Classification Search
CPC ..... C12N 5/0647; C12N 5/0696; A61K 35/28
See application file for complete search history.

(56) References Cited

U.S. PATENT DOCUMENTS

| | | | |
|---|---|---|---|
| 2014/0017212 A1 | 1/2014 | Rebar | |
| 2014/0017214 A1* | 1/2014 | Cost | A61K 38/465 435/325 |
| 2016/0231319 A1* | 8/2016 | Kaplan | C12Q 1/6883 |
| 2016/0369262 A1 | 12/2016 | Reik et al. | |

FOREIGN PATENT DOCUMENTS

| | | |
|---|---|---|
| WO | 2014/036219 A2 | 3/2014 |
| WO | 2018/170184 A1 | 9/2018 |
| WO | 2018/220210 A1 | 12/2018 |
| WO | 2018/220211 A1 | 12/2018 |

OTHER PUBLICATIONS

Cai et al. A universal approach to correct various HBB gene mutations in human stem cells for gene therapy of beta-thalessemia and sickle cell disease. Stem Cells Transl Med 2018, 7(1):87-97. (Year: 2017).*
Dever et al. CRISPR/Cas9 beta-globin gene targeting in human haematopoietic stem cells. Nature 2016, 539:384-389. (Year: 2016).*
Samakoglu et al. A genetic strategy to treat sickle cell anemia by coregulating globin transgene expression and RNA interference. Nature Biotechnology 2006, 24;1:89-94. (Year: 2006).*
Chen et al. Expression of human factor IX in murine plasma through lentiviral vector-infected haematopoietic stem cells. Clinical and Experimental Pharmacology and Physiology 2006, 33;12:1196-1201. (Year: 2006).*
Hardison. Evolution of Hemoglobin and its Genes. Cold Spring Harbor Perspectives in Medicine 2012, 2;a011627: 1-19. (Year: 2012).*
Song et al. Improved hematopoietic differentiation efficiency of gene-corrected beta-thalassemia induced pluripotent stem cells by CRISPR/Cas9 system. Stem Cells and Development 2015, 24;9:1053-1065. (Year: 2015).*
Harding et al. Intravenous administration of an AAV-2 vector for the expression of factor IX in mice and a dog model of hemophilia B. Gene Therapy 2004, 11:204-213. (Year: 2004).*
Akashi et al: "A clonogenic common myeloid progenitor that gives rise to all myeloid lineages", Nature, vol. 404, pp. 193-197, Mar. 9, 2000.
Akhtar et al: "Chromatin Position Effects Assayed by Thousands of Reporters Integrated in Parallel", Cell, vol. 154, pp. 914-927, Aug. 15, 2013.
Bolhassani et al: "In vitro and in vivo delivery of therapeutic proteins using cell penetrating peptides", Peptides, Nov. 21, 2016.
Boutin et al: "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors", Human Gene Therapy, vol. 21, pp. 704-712, Jun. 2010.
Brinkman et al: "Easy quantitative assessment of genome editing by sequence trace decomposition" Nucleic Acids Research, Sep. 24, 2014.

(Continued)

*Primary Examiner* — Allison M Fox
*Assistant Examiner* — Jennifer S Spence
(74) *Attorney, Agent, or Firm* — WCF IP

(57) ABSTRACT

The present invention relates to a genetically modified hematopoietic stem cell comprising, in at least one globin gene comprised in the genome thereof, at least one transgene encoding a therapeutic protein or a therapeutic ribonucleic acid, the said transgene being placed under the control of the endogenous promoter of the said globin gene.

13 Claims, 7 Drawing Sheets
Specification includes a Sequence Listing.

(56) References Cited

OTHER PUBLICATIONS

Carroll: "Genome Engineering With Zinc-Finger Nucleases", Genetics, vol. 188, pp. 773-782, Aug. 2011.
Chang et al: "Stem cell-derived erythroid cells mediate long-term systemic protein delivery", Nature Biotechnology, vol. 24, No. 8, pp. 1017-1021, Aug. 2006.
Chang et al: "Erythroid-specific Human Factor IX Delivery From In Vivo Selected Hematopoietic Stem Cells Following Nonmyeloablative Conditioning in Hemophilia B Mice", Mol Ther. vol. 16, No. 10, pp. 1745-1752, Oct. 2008.
Chung et al: "Human Embryonic Stem Cell Lines Generated without Embryo Destruction" Cell Stem Cell, pp. 113-117, Feb. 2008.
Cong et al: "Multiplex Genome Engineering Using CRISPR/Cas Systems", Science, vol. 339, pp. 819-823, Feb. 15, 2013.
Cremel et al: "Red blood cells as innovative antigen carrier to induce specific immune tolerance", International Journal of Phamaceutics, vol. 443, pp. 39-49, Jan. 7, 2013.
Cremel et al: "Innovative approach in Pompe disease therapy: Induction of immune tolerance by antigen-encapsulated red blood cells", International Journal of Phamaceutics, vol. 491, pp. 69-77, Jun. 6, 2015.
Dever et al: "CRISPS/Cas9 beta-globin gene targeting in human haematopoietic stem cells", Nature, vol. 539, No. 7629, p. 384, Nov. 17, 2016.
Dias et al: "Generation of Red Blood Cells from Human Induced Pluripotent Stem Cells", Stem Cells and Development, vol. 20, No. 9, pp. 1639-1647, 2011.
Domingues et al.: "New agents in HSC mobilization", Int J Hematol, vol. 105, pp. 141-152, 2017.
Grimm et al: "Memory of tolerance and induction of regulatory T cells by erythrocyte-targeted antigens", Scientific Reports, Oct. 29, 2015.
Hargrove et al: "Globin Lentiviral Vector Insertions Can Perturb the Expression of Endogenous Genes in ß-thalassemic Hematopoietic Cells", Molecular Therapy, vol. 16, No. 3, pp. 525-533, Mar. 2008.
Huang et al: "Genetically engineered red cells expressing single domain camelid antibodies confer long-term protection against botulinum neurotoxin", Nature Communications, vol. 8, No. 423, 2017.
Jinek et al: "A Programmable Dual-RNA-Guided DNA Endonuclease in Adaptive Bacterial Immunity", Science, vol. 337, pp. 816-821, Aug. 17, 2012.
Kessinger: "The Nebraska Experience", Stem Cells, vol. 13, pp. 23-27, 1995.
Lapillonne et al: "Red blood cell generation from human induced pluripotent stem cells: perspectives for transfusion medicine", Haematologica, vol. 95, No. 10, pp. 1651-1659, May 17, 2010.
Lawlor et al: "Enzyme replacement therapy rescues weakness and improves muscle pathology in mice with X-linked myotubular myopahty", Human Molecular Genetics, vol. 22, No. 8, pp. 1525-1538, Jan. 9, 2013.
Lorentz et al: "Engineered binding to erythrocytes induces immunological tolerance to E. coli asparaginase", Science Advances, vol. 1, No. 6, Jul. 17, 2015.
Mali et al: "Cas9 as a versatile tool for engineering biology", Nat Methods, vol. 10, No. 10, pp. 957-963, Oct. 2013.
Moiani et al: "Lentiviral vector integration in the human genome induces alternative splicing and generates aberrant transcriptions", The Journal of Clinical Investigation, vol. 122, No. 5, pp. 1653-1666, May 2012.
Montiel-Equiha et al: "Gene Therapy for Severe Combined Immunodeficiency due to Adenosine Deaminase Deficiency", Current Gene Therapy, vol. 12, pp. 57-65, 2012.
Pishesha et al: "Engineered erythrocytes covalently linked to antigenic peptides can protect against autoimmune disease", PNAS, vol. 114, No. 12, pp. 3157-3162, Mar. 21, 2017.
Pishesha et al: "Engineered erythrocytes covalently linked to antigenic peptides can protect against autoimmune disease", PNAS, vol. 114, No. 17, Apr. 25, 2017.
Puzzo et al: "Rescue of Pompe disease in mice by AAV-mediated liver delivery of secretable acid α-glucosidase", Sci Transl Med., vol. 9, No. 418, 2017.
Sadelain et al: "Supplying Clotting Factors From Hematopoietic Stem Cell-derived Erythroid and Megakaryocytic Lineage Cells", Molecular Therapy, vol. 17, No. 12, pp. 1994-1999, Dec. 2009.
Sadelain et al: "Safe harbours for the integration of new DNA in the human genome", Cancer vol. 12, pp. 51-58, Jan. 2012.
Sharma et al: "In vivo genome editing of the albumin locus as a platform for protein replacement therapy", Blood, vol. 126, No. 15, pp. 1777-1784, Oct. 8, 2015.
Urnov et al: "Genome editing with engineered zinc finger nucleases", Genetics, vol. 11, pp. 636-646, Sep. 2010.
Wang et al: "Reprogramming erythroid cells lysosomal enzyme production leads to visceral and CNS cross-correction in mice with Hyrler syndrome", PNAS, vol. 106, No. 47, pp. 19958-19963, Nov. 24, 2009.
Wang et al: "Engineering a lysosomal enzyme with a derivative of receptor-binding domain of apoE enables delivery across the blood-brain barrier", PNAS, vol. 110, No. 8, pp. 2999-3004, Feb. 19, 2013.
Wang et al: "Scalable Production of Human Erythrocytes from Induced Pluripotent Stem Cells", BIORXIV, Apr. 23, 2016.
Wright et al.: "TALEN-mediated genome editing: prospects and perspectives", Biochem J. vol. 462, pp. 15-24, 2014.
Wright et al: "Biology and Applications of CRISPR Systems: Harnessing Nature's Toolbox for Genome Engineering", Cell, vol. 164, pp. 29-44, Jan. 14, 2016.
Ku et al.: "Both TALENs and CRISPE/Cas9 directly target the HBB IVS2-654 (C?>?T) mutation in &bgr;-thalassemia-derived iPSCs", Scientific Reports, vol. 5, p. 12065, Jul. 9, 2015.

* cited by examiner

SEQUENCE LISTING

<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Synthetic Partial nucleic acid sequence of HBA 4
<220> FEATURE:
<223> OTHER INFORMATION: Synthetic Partial nucleic acid sequence of HBA 4

<400> SEQUENCE: 1
ggggcgcggc ctggaccgca                          20

<210> SEQ ID NO 2
<211> LENGTH: 23
<212> TYPE: DNA
<213> ORGANISM: Artificial Sequence
<220> FEATURE:
<223> OTHER INFORMATION: Synthetic Full nucleic acid sequence of HBA 4
<220> FEATURE:
<223> OTHER INFORMATION: Synthetic Full nucleic acid sequence of HBA 4

<400> SEQUENCE: 2
ggggcgcggc ctggaccgca ggg                      23

<210> SEQ ID NO 3
<211> LENGTH: 20
<212> TYPE: DNA
<213> ORGANISM: Artificial Sequence
<220> FEATURE:
<223> OTHER INFORMATION: Synthetic Partial nucleic acid sequence of HBA 10
<220> FEATURE:
<223> OTHER INFORMATION: Synthetic Partial nucleic acid sequence of HBA 10

<400> SEQUENCE: 3
gggtttatgc ttggggcgcg                          20

<210> SEQ ID NO 4
<211> LENGTH: 23
<212> TYPE: DNA
<213> ORGANISM: Artificial Sequence
<220> FEATURE:
<223> OTHER INFORMATION: Synthetic Full nucleic acid sequence of HBA 10
<220> FEATURE:
<223> OTHER INFORMATION: Synthetic Full nucleic acid sequence of HBA 10

<400> SEQUENCE: 4
gggtttatgc ttggggcgcg ggg                      23

<210> SEQ ID NO 5
<211> LENGTH: 20
<212> TYPE: DNA
<213> ORGANISM: Artificial Sequence
<220> FEATURE:
<223> OTHER INFORMATION: Synthetic Partial nucleic acid sequence of HBA 12
<220> FEATURE:
<223> OTHER INFORMATION: Synthetic Partial nucleic acid sequence of HBA 12

<400> SEQUENCE: 5
gactcagaga gaacccacca                          20

<210> SEQ ID NO 6
<211> LENGTH: 23
<212> TYPE: DNA
<213> ORGANISM: Artificial Sequence
<220> FEATURE:
<223> OTHER INFORMATION: Synthetic Full nucleic acid sequence of HBA 12
<220> FEATURE:
<223> OTHER INFORMATION: Synthetic Full nucleic acid sequence of HBA 12

<400> SEQUENCE: 6
gactcagaga gaacccacca tgg                                        23

<210> SEQ ID NO 7
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      14
<220> FEATURE:
<223> OTHER INFORMATION: Synthetic Partial nucleic acid sequence of HBA
      14

<400> SEQUENCE: 7
tgggttctct ctgagtctgt                                            20

<210> SEQ ID NO 8
<211> LENGTH: 23
<212> TYPE: DNA
<213> ORGANISM: Artificial Sequence
<220> FEATURE:
<223> OTHER INFORMATION: Synthetic Full nucleic acid sequence of HBA 14
<220> FEATURE:
<223> OTHER INFORMATION: Synthetic Full nucleic acid sequence of HBA 14

<400> SEQUENCE: 8
tgggttctct ctgagtctgt ggg                                        23

<210> SEQ ID NO 9
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      19.1
<220> FEATURE:
<223> OTHER INFORMATION: Synthetic Partial nucleic acid sequence of HBA
      19.1

<400> SEQUENCE: 9 gcgcggggc acgcccggcc                                             20

<210> SEQ ID NO 10
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      19.1
<220> FEATURE:
<223> OTHER INFORMATION: Synthetic Full nucleic acid sequence of HBA
      19.1

<400> SEQUENCE: 10 gcgcggggc acgcccggcc ggg                                         23

<210> SEQ ID NO 11
<211> LENGTH: 20
<212> TYPE: DNA

<213> ORGANISM: Artificial Sequence
<220> FEATURE:
<223> OTHER INFORMATION: Synthetic Partial nucleic acid sequence of HBA 15.1
<220> FEATURE:
<223> OTHER INFORMATION: Synthetic Partial nucleic acid sequence of HBA 15.1

<400> SEQUENCE: 11
gggttctctc tgagtctgtg                                           20

<210> SEQ ID NO 12
<211> LENGTH: 23
<212> TYPE: DNA
<213> ORGANISM: Artificial Sequence
<220> FEATURE:
<223> OTHER INFORMATION: Synthetic Full nucleic acid sequence of HBA 15.1
<220> FEATURE:
<223> OTHER INFORMATION: Synthetic Full nucleic acid sequence of HBA 15.1

<400> SEQUENCE: 12
gggttctctc tgagtctgtg ggg                                       23

<210> SEQ ID NO 13
<211> LENGTH: 20
<212> TYPE: DNA
<213> ORGANISM: Artificial Sequence
<220> FEATURE:
<223> OTHER INFORMATION: Synthetic Partial nucleic acid sequence of HBA 16.1
<220> FEATURE:
<223> OTHER INFORMATION: Synthetic Partial nucleic acid sequence of HBA 16.1

<400> SEQUENCE: 13
gtcggcagga gacagcacca                                           20

<210> SEQ ID NO 14
<211> LENGTH: 23
<212> TYPE: DNA
<213> ORGANISM: Artificial Sequence
<220> FEATURE:
<223> OTHER INFORMATION: Synthetic Full nucleic acid sequence of HBA 16.1
<220> FEATURE:
<223> OTHER INFORMATION: Synthetic Full nucleic acid sequence of HBA 16.1

<400> SEQUENCE: 14
gtcggcagga gacagcacca tgg                                       23

<210> SEQ ID NO 15
<211> LENGTH: 20
<212> TYPE: DNA
<213> ORGANISM: Artificial Sequence
<220> FEATURE:
<223> OTHER INFORMATION: Synthetic Partial nucleic acid sequence of HBA 17-G
<220> FEATURE:
<223> OTHER INFORMATION: Synthetic Partial nucleic acid sequence of HBA 17-G

<400> SEQUENCE: 15
gcaggagaca gcaccatggt                                           20

<210> SEQ ID NO 16
<211> LENGTH: 23

<212> TYPE: DNA
<213> ORGANISM: Artificial Sequence
<220> FEATURE:
<223> OTHER INFORMATION: Synthetic Full nucleic acid sequence of HBA 17-
      G
<220> FEATURE:
<223> OTHER INFORMATION: Synthetic ull nucleic acid sequence of HBA 17-G

<400> SEQUENCE: 16
gcaggagaca gcaccatggt ggg                                             23

<210> SEQ ID NO 17
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      20.1
<220> FEATURE:
<223> OTHER INFORMATION: Synthetic Partial nucleic acid sequence of HBA
      20.1

<400> SEQUENCE: 17
cataaaccct ggcgcgctcg                                                 20

<210> SEQ ID NO 18
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      20.1
<220> FEATURE:
<223> OTHER INFORMATION: Synthetic Full nucleic acid sequence of HBA
      20.1

<400> SEQUENCE: 18
cataaaccct ggcgcgctcg cgg                                             23

<210> SEQ ID NO 19
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      5.1
<220> FEATURE:
<223> OTHER INFORMATION: Synthetic Partial nucleic acid sequence of HBA
      5.1

<400> SEQUENCE: 19
ttgaatgctc cagccggttc                                                 20

<210> SEQ ID NO 20
<211> LENGTH: 23
<212> TYPE: DNA
<213> ORGANISM: Artificial Sequence
<220> FEATURE:
<223> OTHER INFORMATION: Synthetic Full nucleic acid sequence of HBA 5.1
<220> FEATURE:
<223> OTHER INFORMATION: Synthetic Full nucleic acid sequence of HBA 5.1

<400> SEQUENCE: 20
ttgaatgctc cagccggttc cag                                             23

<210> SEQ ID NO 21
<211> LENGTH: 20
<212> TYPE: DNA
<213> ORGANISM: Artificial Sequence -continued

```
<220> FEATURE:
<223> OTHER INFORMATION: Synthetic Partial nucleic acid sequence of
      gRNA2
<220> FEATURE:
<223> OTHER INFORMATION: Synthetic Partial nucleic acid sequence of
      gRNA2

<400> SEQUENCE: 21
cgggaggctt cgcccaatcc                                                  20

<210> SEQ ID NO 22
<211> LENGTH: 23
<212> TYPE: DNA
<213> ORGANISM: Artificial Sequence
<220> FEATURE:
<223> OTHER INFORMATION: Synthetic Full nucleic acid sequence of gRNA2
<220> FEATURE:
<223> OTHER INFORMATION: Synthetic Full nucleic acid sequence of gRNA2

<400> SEQUENCE: 22
cgggaggctt cgcccaatcc tgg                                              23

<210> SEQ ID NO 23
<211> LENGTH: 20
<212> TYPE: DNA
<213> ORGANISM: Artificial Sequence
<220> FEATURE:
<223> OTHER INFORMATION: Synthetic Partial nucleic acid sequence of
      gRNA3
<220> FEATURE:
<223> OTHER INFORMATION: Synthetic Partial nucleic acid sequence of
      gRNA3

<400> SEQUENCE: 23
cgggcgagcg agtgcgagcc                                                  20

<210> SEQ ID NO 24
<211> LENGTH: 22
<212> TYPE: DNA
<213> ORGANISM: Artificial Sequence
<220> FEATURE:
<223> OTHER INFORMATION: Synthetic Full nucleic acid sequence of gRNA3
<220> FEATURE:
<223> OTHER INFORMATION: Synthetic Full nucleic acid sequence of gRNA3

<400> SEQUENCE: 24
cgggcgagcg agtgcgagcc gg                                               22

<210> SEQ ID NO 25
<211> LENGTH: 20
<212> TYPE: DNA
<213> ORGANISM: Artificial Sequence
<220> FEATURE:
<223> OTHER INFORMATION: Synthetic Partial nucleic acid sequence of
      gRNA11
<220> FEATURE:
<223> OTHER INFORMATION: Synthetic Partial nucleic acid sequence of
      gRNA11

<400> SEQUENCE: 25
gggaggcttc gcccaatcct                                                  20

<210> SEQ ID NO 26
<211> LENGTH: 23
<212> TYPE: DNA
<213> ORGANISM: Artificial Sequence
<220> FEATURE:
<223> OTHER INFORMATION: Synthetic Full nucleic acid sequence of gRNA11
<220> FEATURE:
```

-continued

<223> OTHER INFORMATION: Synthetic Full nucleic acid sequence of gRNA11

<400> SEQUENCE: 26
gggaggcttc gcccaatcct ggg          23

<210> SEQ ID NO 27
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      INT1 72.1
<220> FEATURE:
<223> OTHER INFORMATION: Synthetic Partial nucleic acid sequence of HBA
      INT1 72.1

<400> SEQUENCE: 27
caggccaccc tcaaccgtcc          20

<210> SEQ ID NO 28
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      INT1 72.1
<220> FEATURE:
<223> OTHER INFORMATION: Synthetic Full nucleic acid sequence of HBA
      INT1 72.1

<400> SEQUENCE: 28
caggccaccc tcaaccgtcc tgg          23

<210> SEQ ID NO 29
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      INT1 73.2
<220> FEATURE:
<223> OTHER INFORMATION: Synthetic Partial nucleic acid sequence of HBA
      INT1 73.2

<400> SEQUENCE: 29
tccggggcca ggacggttga          20

<210> SEQ ID NO 30
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      INT1 73.2
<220> FEATURE:
<223> OTHER INFORMATION: Synthetic Full nucleic acid sequence of HBA
      INT1 73.2

<400> SEQUENCE: 30
tccggggcca ggacggttga ggg          23

<210> SEQ ID NO 31
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      INT1 73b.1
<220> FEATURE:

```
<223> OTHER INFORMATION: Synthetic Partial nucleic acid sequence of HBA
      INT1 73b.1

<400> SEQUENCE: 31
gtccggggcc aggacggttg                                                    20

<210> SEQ ID NO 32
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      INT1 73b.1
<220> FEATURE:
<223> OTHER INFORMATION: Synthetic Full nucleic acid sequence of HBA
      INT1 73b.1

<400> SEQUENCE: 32
gtccggggcc aggacggttg agg                                                23

<210> SEQ ID NO 33
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      INT2 13.2
<220> FEATURE:
<223> OTHER INFORMATION: Synthetic Partial nucleic acid sequence of HBA
      INT2 13.2

<400> SEQUENCE: 33
ccctcgaccc agatcgctcc                                                    20

<210> SEQ ID NO 34
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      INT2 13.2
<220> FEATURE:
<223> OTHER INFORMATION: Synthetic Full nucleic acid sequence of HBA
      INT2 13.2

<400> SEQUENCE: 34
ccctcgaccc agatcgctcc cgg                                                23

<210> SEQ ID NO 35
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      INT2 63.2
<220> FEATURE:
<223> OTHER INFORMATION: Synthetic Partial nucleic acid sequence of HBA
      INT2 63.2

<400> SEQUENCE: 35
gaagagggtc agtgcggccc                                                    20

<210> SEQ ID NO 36
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      INT2 63.2
```

```
<220> FEATURE:
<223> OTHER INFORMATION: Synthetic Full nucleic acid sequence of HBA
      INT2 63.2

<400> SEQUENCE: 36
gaagagggtc agtgcggccc agg                                               23

<210> SEQ ID NO 37
<211> LENGTH: 20
<212> TYPE: DNA
<213> ORGANISM: Artificial Sequence
<220> FEATURE:
<223> OTHER INFORMATION: Synthetic Partial nucleic acid sequence of HBA
      INT2 74.1
<220> FEATURE:
<223> OTHER INFORMATION: Synthetic Partial nucleic acid sequence of HBA
      INT2 74.1

<400> SEQUENCE: 37
gcgtgatcct ctgccctgag                                                   20

<210> SEQ ID NO 38
<211> LENGTH: 23
<212> TYPE: DNA
<213> ORGANISM: Artificial Sequence
<220> FEATURE:
<223> OTHER INFORMATION: Synthetic Full nucleic acid sequence of HBA
      INT2 74.1
<220> FEATURE:
<223> OTHER INFORMATION: Synthetic Full nucleic acid sequence of HBA
      INT2 74.1

<400> SEQUENCE: 38
gcgtgatcct ctgccctgag agg                                               23

<210> SEQ ID NO 39
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      37.1
<220> FEATURE:
<223> OTHER INFORMATION: Synthetic Partial nucleic acid sequence of HBB
      37.1

<400> SEQUENCE: 39
gggttggcca atctactccc                                                   20

<210> SEQ ID NO 40
<211> LENGTH: 22
<212> TYPE: DNA
<213> ORGANISM: Artificial Sequence
<220> FEATURE:
<223> OTHER INFORMATION: Synthetic Full nucleic acid sequence of HBB
      37.1
<220> FEATURE:
<223> OTHER INFORMATION: Synthetic Full nucleic acid sequence of HBB
      37.1

<400> SEQUENCE: 40
ggttggccaa tctactccca gg                                                22

<210> SEQ ID NO 41
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
```

```
                                49.2
<220> FEATURE:
<223> OTHER INFORMATION: Synthetic Partial nucleic acid sequence of HBB
      49.2

<400> SEQUENCE: 41
gggttggcca atctactccc                                                    20

<210> SEQ ID NO 42
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      49.2
<220> FEATURE:
<223> OTHER INFORMATION: Synthetic Full nucleic acid sequence of HBB
      49.2

<400> SEQUENCE: 42
gggttggcca atctactccc agg                                                23

<210> SEQ ID NO 43
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      53.1
<220> FEATURE:
<223> OTHER INFORMATION: Synthetic Partial nucleic acid sequence of HBB
      53.1

<400> SEQUENCE: 43
ggagtagatt ggccaaccct                                                    20

<210> SEQ ID NO 44
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      53.1
<220> FEATURE:
<223> OTHER INFORMATION: Synthetic Full nucleic acid sequence of HBB
      53.1

<400> SEQUENCE: 44
ggagtagatt ggccaaccct agg                                                23

<210> SEQ ID NO 45
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      54.1
<220> FEATURE:
<223> OTHER INFORMATION: Synthetic Partial nucleic acid sequence of HBB
      54.1

<400> SEQUENCE: 45
gattggccaa ccctagggtg                                                    20

<210> SEQ ID NO 46
<211> LENGTH: 23
<212> TYPE: DNA
<213> ORGANISM: Artificial Sequence
<220> FEATURE:
```

<223> OTHER INFORMATION: Synthetic Full nucleic acid sequence of HBB
     54.1
<220> FEATURE:
<223> OTHER INFORMATION: Synthetic Full nucleic acid sequence of HBB
     54.1

<400> SEQUENCE: 46
gattggccaa ccctagggtg tgg                                          23

<210> SEQ ID NO 47
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
     77.1
<220> FEATURE:
<223> OTHER INFORMATION: Synthetic Partial nucleic acid sequence of HBB
     77.1

<400> SEQUENCE: 47
gagtagattg gccaaccta                                               20

<210> SEQ ID NO 48
<211> LENGTH: 23
<212> TYPE: DNA
<213> ORGANISM: Artificial Sequence
<220> FEATURE:
<223> OTHER INFORMATION: Synthetic Full nucleic acid sequence of HBB
     77.1
<220> FEATURE:
<223> OTHER INFORMATION: Synthetic Full nucleic acid sequence of HBB
     77.1

<400> SEQUENCE: 48
gagtagattg gccaaccta ggg                                           23

<210> SEQ ID NO 49
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
     INT 1 36.2
<220> FEATURE:
<223> OTHER INFORMATION: Synthetic Partial nucleic acid sequence of HBB
     INT 1 36.2

<400> SEQUENCE: 49
tggtatcaag gttacaagac                                              20

<210> SEQ ID NO 50
<211> LENGTH: 23
<212> TYPE: DNA
<213> ORGANISM: Artificial Sequence
<220> FEATURE:
<223> OTHER INFORMATION: Synthetic Full nucleic acid sequence of HBB
     INT 1 36.2
<220> FEATURE:
<223> OTHER INFORMATION: Synthetic Full nucleic acid sequence of HBB
     INT 1 36.2

<400> SEQUENCE: 50
tggtatcaag gttacaagac agg                                          23

<210> SEQ ID NO 51
<211> LENGTH: 20
<212> TYPE: DNA
<213> ORGANISM: Artificial Sequence

```
<220> FEATURE:
<223> OTHER INFORMATION: Synthetic Partial nucleic acid sequence of HBB
      INT1 36.2 REV
<220> FEATURE:
<223> OTHER INFORMATION: Synthetic Partial nucleic acid sequence of HBB
      INT1 36.2 REV

<400> SEQUENCE: 51
tccacatgcc cagtttctat                                                    20

<210> SEQ ID NO 52
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      INT1 36.2 REV
<220> FEATURE:
<223> OTHER INFORMATION: Synthetic Full nucleic acid sequence of HBB
      INT1 36.2 REV

<400> SEQUENCE: 52
tccacatgcc cagtttctat tgg                                                23

<210> SEQ ID NO 53
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      INT1 47.1
<220> FEATURE:
<223> OTHER INFORMATION: Synthetic Partial nucleic acid sequence of HBB
      INT1 47.1

<400> SEQUENCE: 53
ttaaggagac caatagaaac                                                    20

<210> SEQ ID NO 54
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      INT1 47.1
<220> FEATURE:
<223> OTHER INFORMATION: Synthetic Full nucleic acid sequence of HBB
      INT1 47.1

<400> SEQUENCE: 54
ttaaggagac caatagaaac tgg                                                23

<210> SEQ ID NO 55
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      INT1 48.1
<220> FEATURE:
<223> OTHER INFORMATION: Synthetic Partial nucleic acid sequence of HBB
      INT1 48.1

<400> SEQUENCE: 55
taaggagacc aatagaaact                                                    20

<210> SEQ ID NO 56
<211> LENGTH: 23
<212> TYPE: DNA
```

```
<213> ORGANISM: Artificial Sequence
<220> FEATURE:
<223> OTHER INFORMATION: Synthetic Full nucleic acid sequence of HBB
      INT1 48.1
<220> FEATURE:
<223> OTHER INFORMATION: Synthetic Full nucleic acid sequence of HBB
      INT1 48.1

<400> SEQUENCE: 56
taaggagacc aatagaaact ggg                                              23

<210> SEQ ID NO 57
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      INT2 340.1
<220> FEATURE:
<223> OTHER INFORMATION: Synthetic Partial nucleic acid sequence of HBB
      INT2 340.1

<400> SEQUENCE: 57
ctgcctagta cattactatt                                                  20

<210> SEQ ID NO 58
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      INT2 340.1
<220> FEATURE:
<223> OTHER INFORMATION: Synthetic Full nucleic acid sequence of HBB
      INT2 340.1

<400> SEQUENCE: 58
ctgcctagta cattactatt tgg                                              23

<210> SEQ ID NO 59
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      INT2 797.1
<220> FEATURE:
<223> OTHER INFORMATION: Synthetic Partial nucleic acid sequence of HBB
      INT2 797.1

<400> SEQUENCE: 59
attagcaaaa gggcctagct                                                  20

<210> SEQ ID NO 60
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      INT2 797.1
<220> FEATURE:
<223> OTHER INFORMATION: Synthetic Full nucleic acid sequence of HBB
      INT2 797.1

<400> SEQUENCE: 60
attagcaaaa gggcctagct tgg                                              23

<210> SEQ ID NO 61
<211> LENGTH: 20
```

```
<212> TYPE: DNA
<213> ORGANISM: Artificial Sequence
<220> FEATURE:
<223> OTHER INFORMATION: Synthetic Partial nucleic acid sequence of HBB
      INT2 20.1
<220> FEATURE:
<223> OTHER INFORMATION: Synthetic Partial nucleic acid sequence of HBB
      INT2 20.1

<400> SEQUENCE: 61
gttaagttca tgtcatagga                                                   20

<210> SEQ ID NO 62
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      INT2 20.1
<220> FEATURE:
<223> OTHER INFORMATION: Synthetic ull nucleic acid sequence of HBB
      INT2 20.1

<400> SEQUENCE: 62
gttaagttca tgtcatagga agg                                               23

<210> SEQ ID NO 63
<211> LENGTH: 20
<212> TYPE: DNA
<213> ORGANISM: Artificial Sequence
<220> FEATURE:
<223> OTHER INFORMATION: Synthetic Partial nucleic acid sequence of HBB
      INT2 39.2
<220> FEATURE:
<223> OTHER INFORMATION: Synthetic Partial nucleic acid sequence of HBB
      INT2 39.2

<400> SEQUENCE: 63
gacgaatgat tgcatcagtg                                                   20

<210> SEQ ID NO 64
<211> LENGTH: 23
<212> TYPE: DNA
<213> ORGANISM: Artificial Sequence
<220> FEATURE:
<223> OTHER INFORMATION: Synthetic Full nucleic acid sequence of HBB
      INT2 39.2
<220> FEATURE:
<223> OTHER INFORMATION: Synthetic Full nucleic acid sequence of HBB
      INT2 39.2

<400> SEQUENCE: 64
gacgaatgat tgcatcagtg tgg                                               23

<210> SEQ ID NO 65
<211> LENGTH: 20
<212> TYPE: DNA
<213> ORGANISM: Artificial Sequence
<220> FEATURE:
<223> OTHER INFORMATION: Synthetic Partial nucleic acid sequence of an
      HBB gRNA

<400> SEQUENCE: 65
cttgccccac agggcagtaa                                                   20

<210> SEQ ID NO 66
<211> LENGTH: 23
<212> TYPE: DNA
<213> ORGANISM: Artificial Sequence
```

```
<220> FEATURE:
<223> OTHER INFORMATION: Synthetic Full nucleic acid sequence of a HBB
      gRNA

<400> SEQUENCE: 66
cttgccccac agggcagtaa cgg                                            23

<210> SEQ ID NO 67
<211> LENGTH: 20
<212> TYPE: DNA
<213> ORGANISM: Artificial Sequence
<220> FEATURE:
<223> OTHER INFORMATION: Synthetic partial nucleic acid sequence of an
      AAVS1 gRNA

<400> SEQUENCE: 67
gtcccctcca ccccacagtg                                                20

<210> SEQ ID NO 68
<211> LENGTH: 23
<212> TYPE: DNA
<213> ORGANISM: Artificial Sequence
<220> FEATURE:
<223> OTHER INFORMATION: Synthetic Full nucleic acid sequence of a
      AAVS1 gRNA

<400> SEQUENCE: 68
gtcccctcca ccccacagtg ggg                                            23
```

GENETICALLY ENGINEERED HEMATOPOIETIC STEM CELL AS A PLATFORM FOR SYSTEMIC PROTEIN EXPRESSION

FIELD OF THE INVENTION

The present invention relates to the field of therapeutic treatment by genome engineering.

Notably, the invention relates to a genetically modified hematopoietic stem cell and to its use as a medicament.

BACKGROUND OF THE INVENTION

A number of defects, diseases and pathological conditions in a variety of areas of medicine can be treated by systemic injection of therapeutic proteins. Such therapeutic proteins can indeed compensate for insufficient or non-functional endogenous proteins, bind to a target protein on the surface of a tumour or a virus or bind to a chemical agent such as a toxin, in an individual in need thereof.

Such disorders are potentially addressable via frequent administration of a protein of interest, but more recent methods allow the delivery of nucleic acids encoding therapeutic molecules for treatment of such diseases. The delivery of nucleic acids encoding a therapeutic protein, gene therapy, indeed has the potential to provide significant advantages over conventional therapies requiring the administration of the therapeutic protein per se. Among significant advantages, gene therapy allows a long-term and regulated expression of the therapeutic protein in the cells of a patient. Constant level of protein expression (better pharmacodynamics) results in higher efficiency and lower side effects of the treatment, and the avoidance of toxic and infectious impurities that may otherwise be contained in an administrable protein composition.

The nucleic acids are usually delivered using a vector, most of them being viruses modified in order to remove the original disease-causing genes and replacing them by the nucleic acids encoding the therapeutic molecule(s).

However, this technique also presents many risks, among which the targeting of unintended cells, as viruses are rarely specific to one type of cells; the possibility of insertional mutagenesis and gene transactivation, if the new therapeutic gene is inserted randomly in the cell's DNA; an unwanted immune response against proteins of the said viruses, which can lead to inflammation and destruction of the infected cells; and, in some cases, the virus manages to recover its original ability to cause a disease once it is introduced into the body of the individual.

This technique further presents many disadvantages. For examples, when AAV and adenovirus are used for delivering the transgene of interest, the lack of robust episome replication may limit the duration of expression in mitotically active tissues. Moreover, although transgene integration avoids replication-driven loss, it does not prevent eventual silencing of the exogenous promoter fused to the transgene. Over time, such silencing results in reduced transgene expression for the majority of random insertion events. In addition, integration of a transgene rarely occurs in every target cell, which can make it difficult to achieve a high enough expression level of the transgene of interest to achieve the desired therapeutic effect.

In recent years, a new strategy for transgene integration has been developed that uses genomic DNA cleavage with site-specific nucleases to bias insertion into a chosen locus. One approach involves the integration of a transgene into its cognate locus, for example, insertion of a wild type transgene into the endogenous locus to correct a mutant gene. Alternatively, the transgene may be inserted into a non-cognate locus chosen specifically for its beneficial properties, such as permanent, safe, and very high levels of transgene expression. Illustratively, Sharma et al. (Blood, 2015; 126(15), 1777-1784) achieved integration of FVIII transgene within the albumin gene by using Zing Finger nuclease approach, in liver by in vivo AAV delivery.

In order to allow a safer and more controlled treatment, cells can be infected ex vivo or in vitro with the nucleic acids encoding the therapeutic peptide of interest. These cells can then be administered to the individual in need thereof and play the role of gene delivery systems (see for example patent application WO1999056785).

While interesting, genome editing is still restrained by various limitations, such as: the presence of antibody against AAV capsid and pre-existing liver damage, which precludes treatment to a significant portion of patients (Boutin S. et al., Hum. Gene Ther., 2010; 21(6): 704-712); the long-term expression of synthetic nucleases in vivo, which could result in toxic unintended genomic cleavage and potentially trigger immune responses against transduced hepatocytes.

Moreover, while a typical genome editing approach is to target the disease locus itself, it can lead to level of proteins insufficient to alleviate the disease phenotype due to low numbers of corrected alleles. For overcoming such a limitation, nucleic acids encoding the therapeutic molecule(s) of interest can be integrated into a genome locus endowed with a high transcriptional activity and "safe" in term of perturbing endogenous gene activity (Sadelain et al., Nat. Rev. Cancer, 2011 Dec. 1; 12(1):51-8).

As normal hematopoiesis yields $2.4.10^{11}$ red blood cells per day in a healthy individual, it has been proposed to redirect a fraction of the globin-synthesis capacity of maturing erythroid cells (~7.2 gr/day) to the production of secreted proteins without interfering with the normal function and homeostasis of the red blood cells.

Due to the high number of expressing erythroid cells and the strong transcriptional potential of the globin promoter, even the correction of a small number of erythroblast (<7%; A. H. Chang et al., Molecular Therapy. 16, 1745-1752 (2008); M. Sadelain et al., Molecular Therapy. 17, 1994-1999 (2009); A. H. Chang Nat Biotechnol. 24(8):1017-21 (2006)) resulted in strong FIX transgene expression levels, above the therapeutic threshold, providing a clinical benefit for haemophilia B. In addition, erythroid restricted FIX expression was also able to induce immune tolerance to FIX in treated mice, even after protein challenge.

Following this idea, immune tolerization has also been reported for erythroid expression of adenosine deaminase, α-L-iduronidase and antibodies (C. A. Montiel-Equihua, A. J. Thrasher, Curr. gene Ther. 2012 Feb. 1; 12(1):57-65 and D. Wang et al., Proc. Natl. Acad. Sci. U.S.A. 2009 and 2013; Huang N. J. Nat Commun. 8(1):423. (2017)).

Although these approaches have a potential clinical applicability, they all face the same drawbacks associated with the use of viral vector for delivery and integration of the therapeutic transgene:

i) the risk of insertional mutagenesis mainly associated with gene inactivation and generation of aberrant/chimeric transcripts at integration sites (A. Moiani et al., J. Clin. Invest. 122, 1653-1666 (2012)) and of transcriptional transactivation of neighbouring genes when strong enhancer/promoter elements are present (P. W. Hargrove et al., Molecular Therapy, 16, 525-533 (2008)); and ii) the limits of artificial promoters, which can only partially reproduce the physiological complex regulation of endogenous ones due to delivery vector contrains (e.g. size limitations) and integration in different chromatin context, resulting in unpredictable expression patterns (W. Akthar et al., Cell, 154, 914-927 (2013)).

There is thus a need for designing a novel safe therapeutic platform allowing high transcription of any therapeutic protein or therapeutic ribonucleic acid of interest in a sufficiently high level to alleviate the disease to be treated.

SUMMARY OF THE INVENTION

A first object of the present invention relates to a genetically modified hematopoietic stem cell comprising, in at least one globin gene comprised in the genome thereof, at least one transgene encoding a therapeutic protein or a therapeutic ribonucleic acid, the said transgene being placed under the control of the endogenous promoter of the said at least one globin gene.

In a particular embodiment, the at least one transgene encoding a therapeutic protein or a therapeutic ribonucleic acid is comprised in the 5' region, in the 3' untranslated region and/or in an intron of the said at least one globin gene. More particularly, the at least one transgene encoding a therapeutic protein or a therapeutic ribonucleic acid can be comprised in the 5' untranslated region (5' UTR) and/or in the proximal promoter and/or in the second intron (IVS2) of the said at least one globin gene, preferably can be comprised in the 5' untranslated region (5' UTR) or in the proximal promoter or in the second intron (IVS2) of the said at least one globin gene.

In another particular embodiment, the at least one globin gene comprised in the genome of the said hematopoietic stem cell is selected from the group consisting of the epsilon globin gene, the gamma G globin gene, the gamma A globin gene, the delta globin gene, the beta globin gene, the zeta globin gene, the pseudozeta globin gene, the mu globin gene, the pseudoalpha-1 globin gene, the alpha 1 globin gene and the alpha 2 globin gene, in particular selected from the group consisting of the gamma G globin gene, the gamma A globin gene, the delta globin gene, the beta globin gene, the alpha 1 globin gene and the alpha 2 globin gene, more particularly selected from the group consisting of the alpha 1 globin gene and the alpha 2 globin gene.

In a further embodiment, the encoded therapeutic protein is selected from the group consisting of cytokines, in particular interferon, more particularly interferon-alpha, interferon-beta or interferon-pi; hormones; chemokines; antibodies (including nanobodies); anti-angiogenic factors; enzymes for replacement therapy, such as for example adenosine deaminase, alpha glucosidase, alpha-galactosidase, alpha-L-iduronidase (also name idua) and beta-glucosidase; interleukins; insulin; G-CSF; GM-CSF; hPG-CSF; M-CSF; blood clotting factors such as Factor VIII, Factor IX or tPA; transmembrane proteins such as Nerve Growth Factor Receptor (NGFR); lysosomal enzymes such as α-galactosidase (GLA), α-L-iduronidase (IDUA), lysosomal acid lipase (LAL) and galactosamine (N-acetyl)-6-sulfatase (GALNS); any protein that can be engineered to be secreted and eventually uptaken by non-modified cells (for example Lawlor M W, Hum Mol Genet. 22(8): 1525-1538. (2013); Puzzo F, Sci Transl Med. 29; 9(418) (2017); Bolhassani A. Peptides. 87:50-63., (2017)) and combinations thereof, and preferably is a blood clotting factor, more preferably Factor VIII; or a lysosomal enzyme, in particular lysosomal acid lipase (LAL) or galactosamine (N-acetyl)-6-sulfatase (GALNS).

Another object of the present invention relates to a genetically modified hematopoietic stem cell comprising, in the intergenic regions flanking at least one globin gene comprised in the genome thereof, at least one transgene encoding a therapeutic protein or a therapeutic ribonucleic acid, the said transgene being placed under the control of the endogenous promoter of the said at least one globin gene.

According to this embodiment, the at least one globin gene and the encoded therapeutic protein can be as defined above.

In another embodiment, the stem cell described herein is a mammalian cell, in particular a human cell.

Another object of the present invention relates to a blood cell originating from a genetically modified hematopoietic stem cell as described herein.

Accordingly, in a particular embodiment, the said blood cell is selected from the group consisting of megakaryocytes, thrombocytes, erythrocytes, mast cells, myeloblasts, basophils, neutrophils, eosinophils, monocytes, macrophages, natural killer cells, small lymphocytes, T lymphocytes, B lymphocytes, plasma cells, and all their precursors.

A further object of the present invention is a pharmaceutical composition comprising at least one genetically modified hematopoietic stem cell as described herein and/or at least one blood cell as described herein, in a pharmaceutically acceptable medium.

Another object of the invention is a method for the in vivo, ex vivo or in vitro preparation, in particular ex vivo or in vitro preparation, of a hematopoietic stem cell as described herein, the method comprising the steps of:

(i) providing to the said stem cell a site-directed genetic engineering system by:
  (a) providing to the said stem cell (1) at least one guide nucleic acid binding to a selected target site or (2) a guide peptide-containing endonuclease binding to a selected target site, the said target site being located in an endogenous globin-encoding gene comprised in the genome of the said hematopoietic stem cell;
  (b) when the at least one guide nucleic acid has been provided at step a), further providing to the said stem cell at least one endonuclease devoid of target site specificity; and
  (c) further providing to the said stem cell a transgene that encodes at least one therapeutic protein or at least one therapeutic ribonucleic acid;
and
(ii) culturing the stem cell obtained at the step (i) such that the said transgene is introduced at the said selected target site in the genome of the said hematopoietic stem cell.

In a particular embodiment, the said target site is located in the 5' region, in the 3' untranslated region (3' UTR) and/or in an intron of the said at least one globin gene, preferably in the 5' untranslated region (5' UTR) and/or in the proximal promoter and/or in the second intron (IVS2) of the said at least one globin gene, in particular in the 5' untranslated region (5' UTR) or in the proximal promoter or in the second intron (IVS2) of the said at least one globin gene.

In another embodiment, the method comprises the steps of:

(i) providing to the said stem cell a site-directed genetic engineering system by:
  (a) providing to the said stem cell at least one guide nucleic acid binding to a selected target site, the said target site being located in an endogenous globin-encoding gene comprised in the genome of the said hematopoietic stem cell;
(b) further providing to the said stem cell at least one endonuclease devoid of target site specificity; and
(c) further providing to the said stem cell a transgene that encodes at least one therapeutic protein or at least one therapeutic ribonucleic acid;
and
(ii) culturing the stem cell obtained at the step (i) such that the said transgene is introduced at the said selected target site in the genome of the said hematopoietic stem cell.

In a particular embodiment, the at least one endonuclease devoid of target site specificity is a Clustered regularly interspaced short palindromic repeats (CRISPR) associated protein (Cas), in particular the CRISPR associated protein 9 (Cas9).

In a particular embodiment, the one or more guide nucleic acid is a guide RNA which recognizes a target site in the 5' region, in the 3' untranslated region (3'UTR) and/or in an intron, preferably in the 5' untranslated region (5' UTR) and/or in the proximal promoter and/or in the second intron (IVS2) of the said at least one globin gene, in particular is comprised in the 5' untranslated region (5' UTR) or in the proximal promoter or in the second intron (IVS2) of at least one of the alpha globin genes comprised in the genome of the hematopoietic stem cell, preferably is comprised in the 5' untranslated region (5' UTR) or in the second intron (IVS2) of at least one of the alpha globin genes comprised in the genome of the hematopoietic stem cell.

Another object of the present invention relates to a hematopoietic stem cell as described herein, or a blood cell as described herein, or a pharmaceutical composition as described herein, for its use as a medicament.

The present invention also relates to a hematopoietic stem cell as described herein, a blood cell as described herein, or a pharmaceutical composition as described herein, for use in the treatment of:
a disease selected from the group consisting of autoimmune diseases, viral infections and tumors; and/or
a disease caused by the lack of a protein or by the presence of an aberrant non-functional one in an individual in need thereof.

According to a particular embodiment, disease caused by the lack of a protein or by the presence of an aberrant non-functional one can be selected from the group consisting of a coagulation disorder, a lysosomal storage disorder, an hormonal defect and an alpha-1 antitrypsin deficiency.

In particular, the individual in need thereof can be a mammal, more particularly can be a human being.

Another object of the present invention relates to a method for producing a transgenic non-human mammal comprising administering a hematopoietic stem cell as described herein, a blood cell as described herein, or a pharmaceutical composition as described herein to said mammal.

In a particular embodiment, a transgenic non-human mammal of the invention encodes a human transgene. Additionally, the transgenic animal may be knocked out at the corresponding endogenous locus, allowing the development of an in vivo system where the human protein may be studied in isolation.

A transgenic non-human mammal according to the invention may be used for screening purposes to identify small molecule, large biomolecules or other entities, which may interact or modify the human protein of interest. In other aspects, the transgenic non-human mammal may be used for production purposes, for example, to produce antibodies or other biomolecules of interest.

Figure 1:
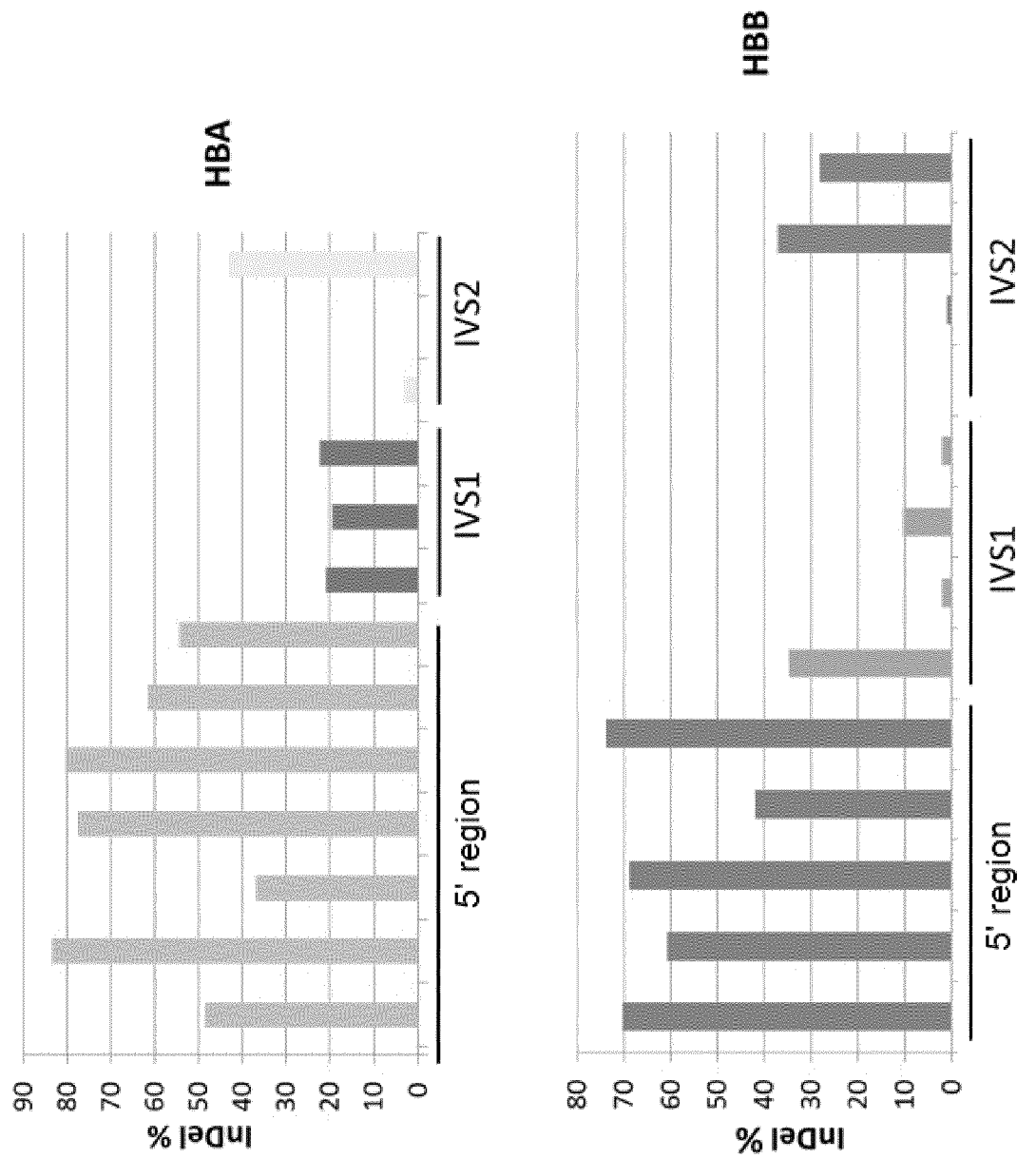
FIG. 1 Design and validation of gRNAs in K562 erythroleukemia cell line

Plasmids expressing different gRNA for HBA or HBB were transfected in K562 cells stabling expressing SpCas9 and their DNA cutting activity was measured with TIDE software (Tracking of InDels by Decomposition—Brinkman et al. Nucleic Acids Res. 2014. 42(22):e168); www.tide.calculator.nk). The activity is represented in FIG. 1 as InDel %, i.e. percentage of modified alleles, for each gRNA tested independently either in the 5' region of the gene as further defined (in particular the 5' UTR of HBA and the proximal promoter of HBB), in intron 1 (IVS1—for Intervening Sequence 1) or in intron 2 (IVS2) of the said gene. The closer to 100% a InDel %, the more efficient the gRNA tested.

Abscissa: the region targeted by the tested gRNA: 5' region, IVS1 or IVS2; each bar represents a different gRNA.

Ordinate: the InDel %.

Figure 2:
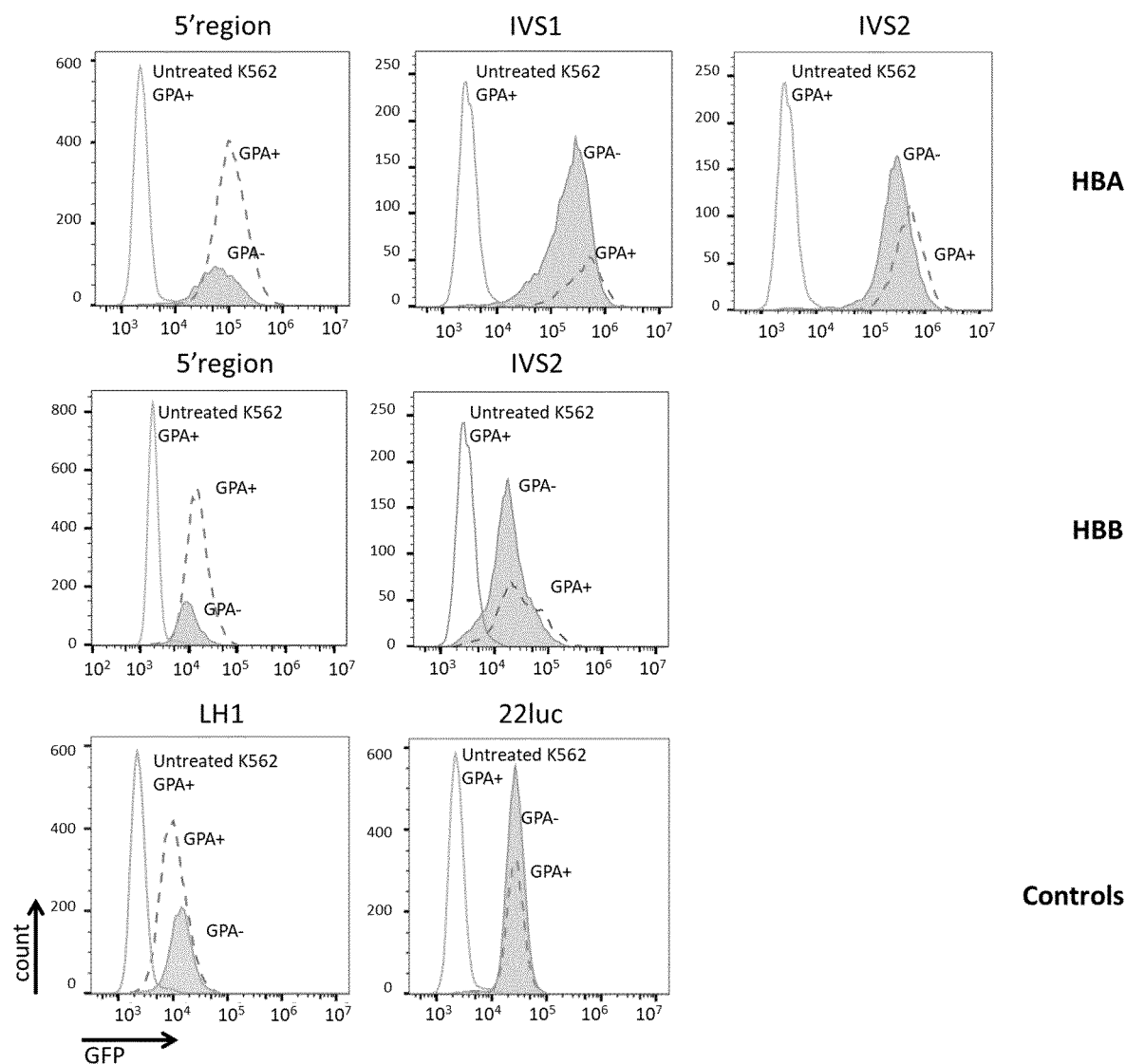

FIG. 2 Targeted integration in HBA and HBB locus of a transgene enables endogenous promoter regulation of the said transgene This Figure illustrated hijacking of HBA and HBB promoter for transgene expression. GFP FACS analyses of K562 with GFP targeted integration in different domain (5' region (5'UTR of HBA or proximal promoter of HBB), IVS1 or IVS2) of HBA or HBB gene. K562 cells were differentiated towards the erythroid lineage.

GFP expression (abscissa) of Glycophorin A (GYPA) positive (dotted line) or GYPA negative (filled histogram) K562 cells are represented.

Controls are cells in which GFP integration is in unrelated genomic locations (not globin genes).

In all panels, untreated GYPA positive K562 cells are shown as a reference (open histogram).

Ordinate: the number of cells.

Figure 3:
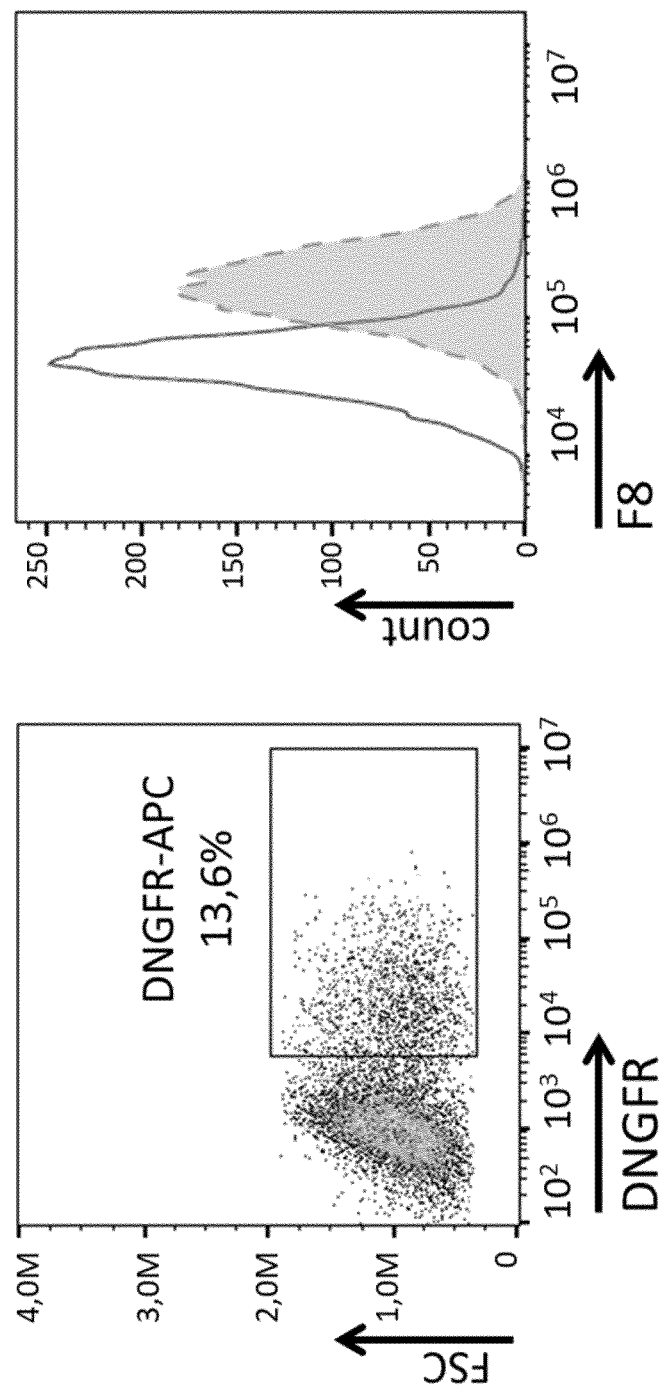

FIG. 3 Targeted integration of a donor DNA in HBA allows stable expression of different transgenes This Figure illustrates that targeted integration of a donor DNA in HBA allows stable expression of different transgenes.

Left panel: Puromycin-selected cells were stained with anti-NGFR (mouse anti human CD271-APC, Miltenyi Biotec) and analysed by flow cytometry. The gate indicates NGFR positive cells.

Ordinate: Forward Scatter (FSC)

Right panel: F8 expression (abscissa) of a representative clone that integrated the F8-puromycin trap in the 5' region (in particular the 5'UTR) of the HBA gene (tinted histogram with dotted line). Control staining of K562 is shown (open histogram).

Ordinate: the number of cells.

Figure 4:
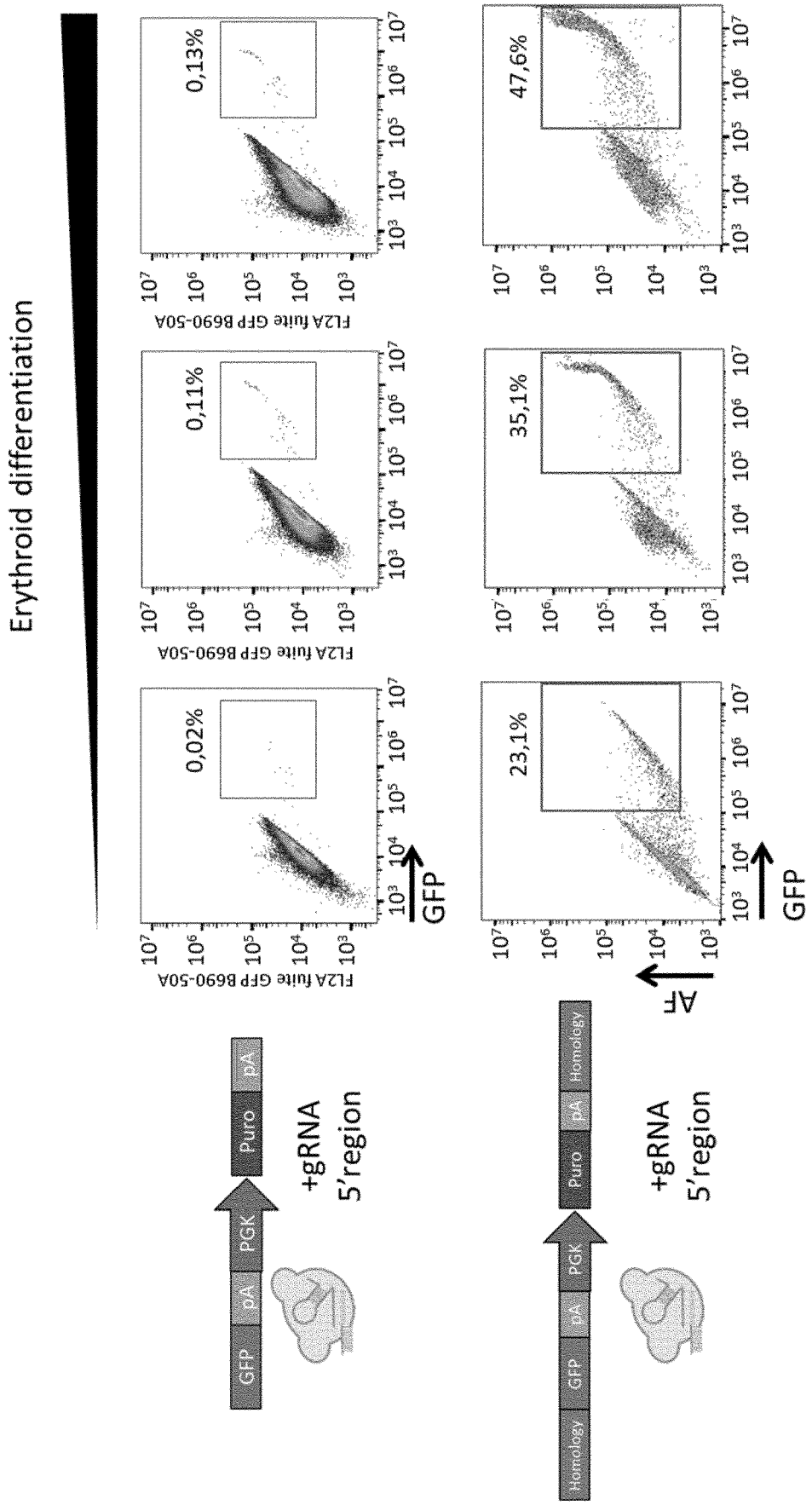

FIG. 4 Effect of homology arms on target integration efficiency in hematopoietic stem/progenitor cells Targeted integration of a GFP-puromycin trap in HBA 1 and 2 in primary HSPC. The insertion of a promoterless GFP cassette in the 5' region of HBA 1 or 2 (in particular the 5'UTR of HBA 1 or 2) either by non-homologous end joining (NHEJ, top panel) or Homology-directed repair (HDR, lower panel) results in regulated GFP expression. GFP positive cells and fluorescence intensity increase along erythroid differentiation recapitulating alpha-globin expression pattern. The addition of homology arms to the donor DNA trap dramatically increases its target integration efficiency.

Ordinate: auto fluorescence channel (AF)

Figure 5:
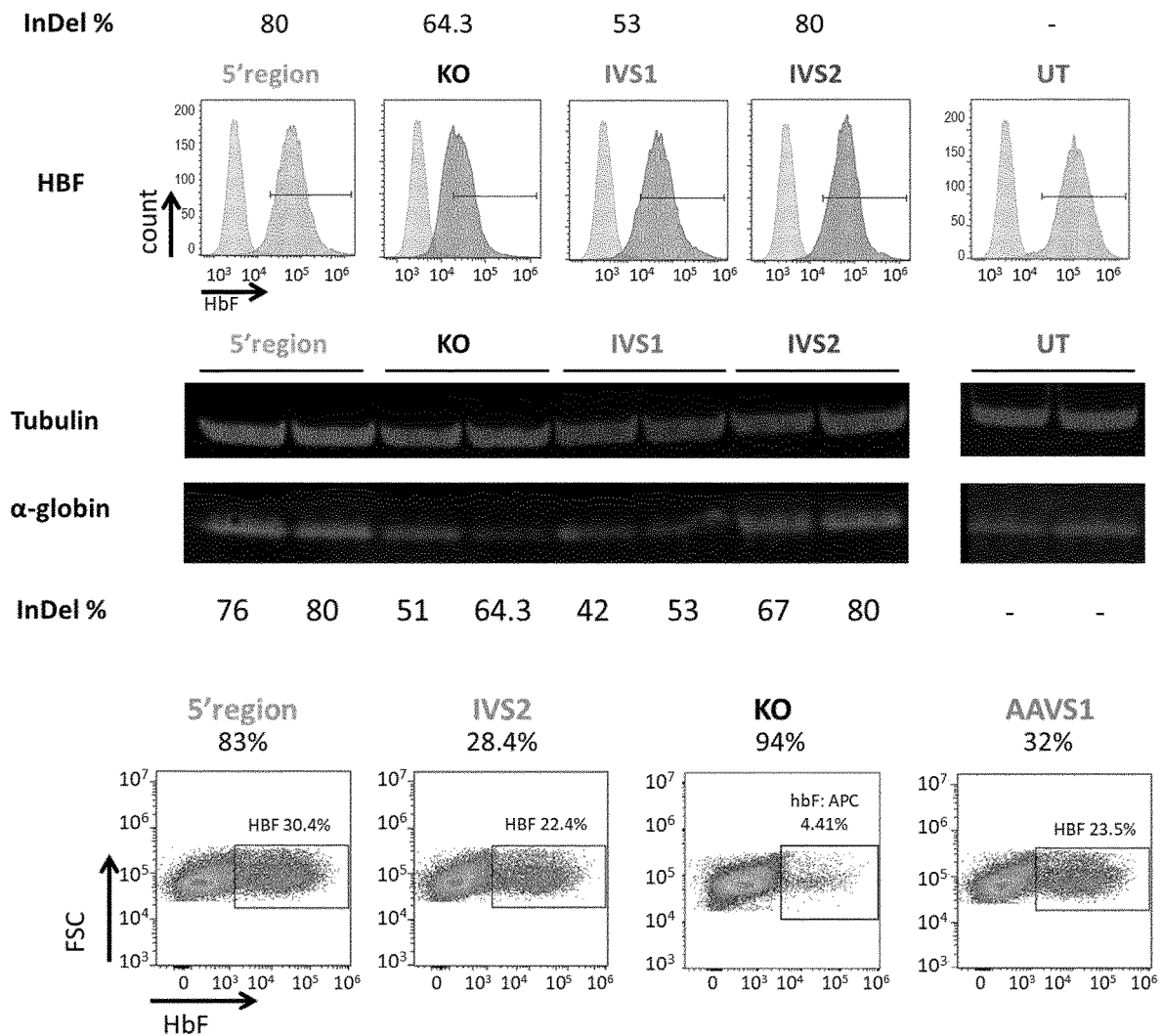

FIG. 5 Effect of on-target activity of each gRNA on HBA production in K562 Histograms of fetal hemoglobin (HbF) expression (abscissa) in K562 cells after genome editing at the indicated sites of HBA. Percentage of modified alleles (InDel %) is indicated on top. As fetal hemoglobin is formed by 2 alpha and 2 gamma subunits, its expression is directly proportional to alpha globin levels in these cells. The control gRNA (KO) targets the first exon of HBA 1 and 2 generating a frameshift mutation that knocks out the gene and affects HbF expression.

Ordinate: number of cells.

On the medium panel, alpha-globin expression is analyzed by western blot on the same cells. 30 pg of total protein was loaded per lane; tubulin was used as loading control. Genome editing efficiencies at specific sites of the HBA genes are indicated below the lanes as percentage of edited alleles (InDel).

On the lower panel, mobilized peripheral blood HSPC were nucleofected with gRNA targeting the indicated sites in the HBA and differentiated towards the erythroid lineage to activate globin expression. Percentage of modified alleles (InDel %) is indicated on top. Expression of HbF (reflecting alpha globin expression; abscissa) at the end of erythroid differentiation for each gRNA tested.

Ordinate: Forward Scatter (FSC)

Figure 6:
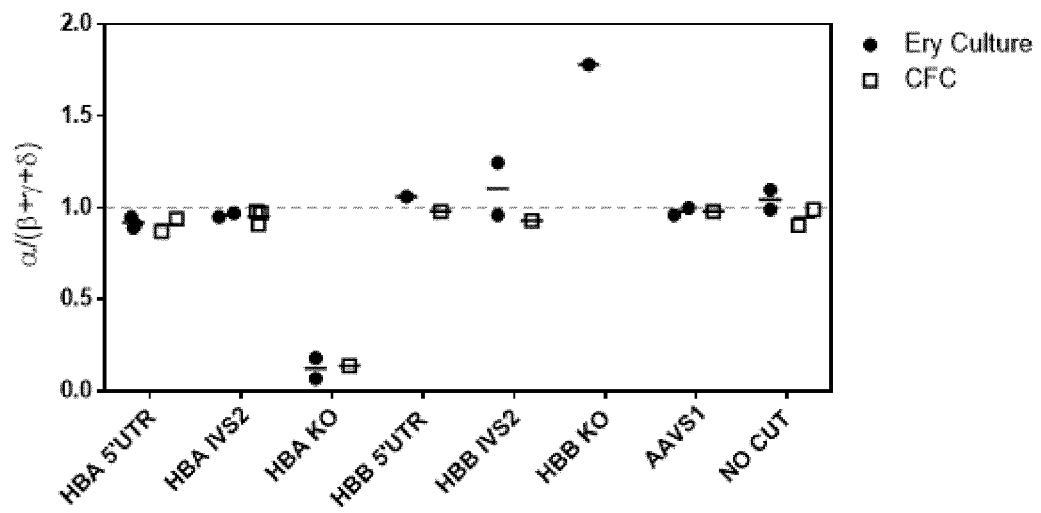

FIG. 6 Effect of editing on the synthesis of HBA and HBB in HSPC derived erythroblasts This Figure illustrates the effect of gRNA targeting different specific sites in the HBA or HBB genes on HBA or HBB synthesis in erythroblasts.

Mobilized peripheral blood HSPC were nucleofected with gRNA targeting different specific sites in the HBA or HBB genes and differentiated towards the erythroid lineage to activate globin expression.

HSPC-derived erythroblasts were lysed and hemoglobin subunits content was measured by chromatography.

The graph represents the ratio between alpha-chain and beta-like chains. In healthy donor cells, this ratio is close to 1 (dashed line and no cut sample), while significant deviations indicate a thalassemia phenotype (<1 in alpha-thalassemic erythroblasts and >1 in beta-thalassemic erythroblasts).

As controls, thalassemic cells were generated using HBA and HBB KO guide RNA, which target the first exon of HBA1/2 and HBB, respectively, and abolish chain expression.

In abscissa, the results correspond, from left to right:
to a gRNA targeting the 5' UTR of HBA (HBA 5'UTR);
to a gRNA targeting the second intron of HBA (HBA IVS2);
to a gRNA targeting the first exon of HBA (HBA KO);
to a gRNA targeting the 5' UTR of HBB (HBB 5'UTR);
to a gRNA targeting the second intron of HBB (HBB IVS2);
to a gRNA targeting the first exon of HBB (HBB KO);
to a gRNA targeting the unrelated AAVS1 locus as control (AAVS1);
to no gRNA no nucleofection control cells (NO CUT).

Ordinate: ratio between alpha-chain and beta-like chains (beta, gamma and delta globin).

In this Figure, "Ery culture" and "CFC" designate the results obtained, respectively, with the liquid culture (HSPC cultured for 14 days in erythroid differentiation medium) or with the red culture (HSPC cultured in semisolid Methocult medium (H4435, StemCell Technologies) for 14 days for colony-forming cells (CFC) assay).

Figure 7:
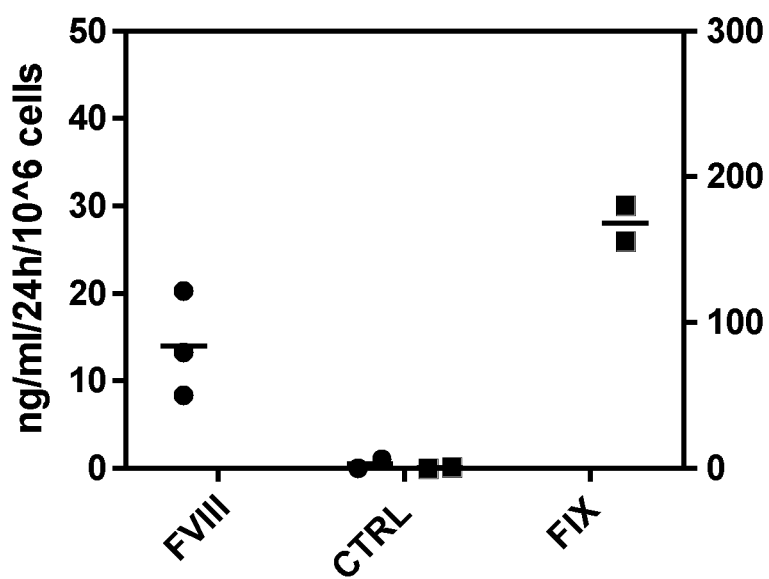

FIG. 7: Targeted integration of Factor VIII (FVIII) or Factor IX (FIX) coding sequence in HBA allows stable expression of these transgenes This Figure illustrates that targeted integration of the coding sequences of FVIII or FIX in HBA of K562 cells allows stable expression and secretion of functional proteins by exploiting the transcriptional control of the endogenous α-globin promoter.

The graph shows the activity of FVIII and FIX secreted in the supernatant of different K562 cells clones. Supernatant of untreated cells was used as control, (CTRL).

Ordinate: activity levels measured as ng/ml of protein per 24 h per 10 cells.

Abscissa: from left to right: results obtained for Factor VIII (FVIII), results obtained with the control (CTRL) and results obtained for Factor IX (FIX).

DETAILED DESCRIPTION OF THE INVENTION

The present inventors managed to generate genetically modified hematopoietic stem cells that, when differentiated towards the erythroid lineage, are able to produce one or more therapeutic protein(s) or one or more therapeutic ribonucleic acid(s) encoded by at least one transgene comprised in at least one globin gene comprised in the genome thereof, in particular in one of its globin gene, placed under the control of the endogenous promoter of the said globin gene. As shown herein, the said therapeutic protein(s) is (are) expressed at a high level, which allows obtaining therapeutic levels of the therapeutic protein or therapeutic ribonucleic acid.

The genetically modified hematopoietic stem cells as described herein advantageously provide a controlled high expression of the therapeutic protein or therapeutic ribonucleic acid of interest.

Another important advantage provided by the present invention, and illustrated in the present examples, is that it does not affect the overall globin expression level in term of hemoglobin or single globin chains.

The use of an ex vivo or in vitro generated hematopoietic stem cell as described herein by transgene targeted integration in the safe globin locus advantageously minimizes the risk of insertional mutagenesis and oncogene transactivation associated with the use of semi-random integrating vectors and the risk of gene transactivation, as no exogenous promoter/enhancer elements are required for transgene expression and inserted in the genome.

Moreover, administration of the hematopoietic stem cells (HSC) as described herein to an individual in need thereof will allow for a long-term correction of diseases of interest considered in the present text by restoring or providing additional function to these stem cells in the said individual.

This method is highly advantageous to the individual in need thereof, as most of the current treatments for the diseases considered herein consist in frequent injections of the therapeutic protein, which is demanding, expensive, not curative on the long term and leads to the development of anti-protein neutralizing antibodies in a high percentage of the treated patients.

For example, when considering diseases caused by the lack of a protein or by the presence of an aberrant non-functional protein in an individual in need thereof, most of the current treatments consist in frequent injections of the said lacking or non-functional protein ("protein replacement therapy"; for example, three injections a week for factor VIII (FVIII) in Hemophilia A). Similarly, lysosomal storage disorders patients necessitate frequent injections to compensate for the mis-functioning enzyme, usually through intravenous injection in large doses. Such treatment is only symptomatic and not curative, thus the patients must undergo repeated administration of these proteins for the rest of their life, and potentially may develop neutralizing antibodies to the injected protein. These proteins often have a short serum half-life, and so the patients must endure frequent infusions of the protein.

Treatment based on the administration of a hematopoietic stem cell as described herein results on the contrary in a limited number of repeated administrations or even in a one-time curative treatment with two major benefits: it will significantly improve the quality of life of the patients and their family and it will reduce the economic cost and burden on the national health system related to the treatment of these most often life-long diseases (for example, a lifetime treatment of a patient with recombinant FVIII costs US $25-50 millions).

Furthermore, administration of the mature blood cells originating from the hematopoietic stem cells as described herein to an individual in need thereof may allow inducing an immune tolerance to the protein encoded by the transgene as described herein.

As also illustrated in the examples of the present text, the inventors managed to identify integration sites that provide a high and erythroid-specific expression of the transgene, without affecting the overall globins expression level in term of hemoglobin or single globin chains.

Genetically Modified Hematopoietic Stem Cells

As indicated above, the present invention firstly relates to a genetically modified hematopoietic stem cell comprising, in at least one globin gene comprised in the genome thereof, at least one transgene encoding a therapeutic protein or a therapeutic ribonucleic acid, the said transgene being placed under the control of the endogenous promoter of the said at least one globin gene.

Hematopoietic stem cells (HSC) are pluripotent stem cells capable of self-renewal and are characterized by their ability to give rise under permissive conditions to all cell types of the hematopoietic system. Hematopoietic stem cells are not totipotent cells, i.e. they are not capable of developing into a complete organism.

In a particular embodiment, a hematopoietic stem cell according to the invention is derived from an embryonic stem cell, in particular from a human embryonic stem cell, and is thus an embryonic hematopoietic stem cell.

Embryonic stem cells (ESCs) are stem cells derived from the undifferentiated inner mass cells of an embryo and capable of self-renewal. Under permissive conditions, these pluripotent stem cells are capable of differentiating in any one of the more than 220 cell types in the adult body. Embryonic stem cells are not totipotent cells, i.e. they are not capable of developing into a complete organism. Embryonic stem cells can for example be obtained according to the method indicated in Young Chung et al. (Cell Stem Cell 2, 2008 Feb. 7; 2(2):113-7.

In another particular embodiment, a hematopoietic stem cell according to the invention is an induced pluripotent stem cell, more particularly a human induced pluripotent stem cell (hiPSCs). Thus, according to a particular embodiment, hematopoietic stem cells as described herein are hematopoietic induced pluripotent stem cells.

Induced pluripotent stem cells are genetically reprogrammed adult cells that exhibit a pluripotent stem cell-like state similar to embryonic stem cells. They are artificially generated stem cells that are not known to exist in the human body but show qualities similar to those of embryonic stem cells. Generating such cells is well known in the art as discussed in Ying WANG et al. (https://doi.org/10.1101/050021) as well as in Lapillonne H. et al. (Haematologica. 2010; 95(10)) and in J. DIAS et al. (Stem Cells Dev. 2011; 20(9):1639-1647).

"Self renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell can divide and form one daughter stem cell and another daughter cell committed to differentiation in the myeloid or lymphoid pathway. Self-renewal provides a continual source of undifferentiated stem cells for replenishment of the hematopoietic system.

The marker phenotypes useful for identifying HSCs will be those commonly known in the art. For human HSCs, the cell marker phenotypes preferably include any combination of $CD34^+CD38^{low/-}Cd49f^+$ $CD59^+$ $CD90^+$ $CD45RA^-$ $Thy1^+$ $C-kit^+$ $lin^-$ (Notta F, Science. 333(6039):218-21 (2011)). For mouse HSCs, the cell marker phenotypes can illustratively be any combination of $CD34^{low/-}$ $Sca-1^+$ $C-kit^+$ and $lin^-$ $CD150^+$ $CD48^-$ $CD90.1.Thy1^{+/low}$ $Flk2/flt3^-$ and $CD117^+$, (see, e.g., Frascoli et al. (J. Vis. Exp. 2012 Jul. 8; (65). Pii:3736.).

Stem cells as described herein are preferably purified. The same applies for blood cells as defined herein.

Many methods for purifying hematopoietic stem cells are known in the art, as illustrated for example in EP1687411.

As used herein, "purified hematopoietic stem cell" or "purified blood cells" means that the recited cells make up at least 50% of the cells in a purified sample; more preferably at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 7⁸%, 79%, 80%, 81%, 82%, 83%, 84%, 85%, 86%, 87%, 88%, 89%, 90%, 91%, 92%, 93%, 94%, 95%, 96%, 97%, 98%, 99%, or more of the cells in a purified sample.

The cells' selection and/or purification can include both positive and negative selection methods to obtain a substantially pure population of cells.

In one aspect, fluorescence activated cell sorting (FACS), also referred to as flow cytometry, can be used to sort and analyze the different cell populations. Cells having the cellular markers specific for HSC or a progenitor cell population are tagged with an antibody, or typically a mixture of antibodies, that binds the cellular markers. Each antibody directed to a different marker is conjugated to a detectable molecule, particularly a fluorescent dye that can be distinguished from other fluorescent dyes coupled to other antibodies. A stream of stained cells is passed through a light source that excites the fluorochrome and the emission spectrum from the cells detects the presence of a particular labelled antibody. By concurrent detection of different fluorochromes, cells displaying different sets of cell markers are identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and progenitor cells is described in, among others, Akashi, K. et al., Nature 404(6774):193-197 (2000)).

In another aspect, immunomagnetic labelling can be used to sort the different cell population. This method is based on the attachment of small magnetizable particles to cells via antibodies or lectins. When the mixed population of cells is placed in a magnetic field, the cells that have beads attached will be attracted by the magnet and may thus be separated from the unlabeled cells.

In a particular embodiment, a modified hematopoietic stem cell as described herein is a mammalian cell and in particular a human cell.

In a particular embodiment, the initial population of hematopoietic stem cells and/or blood cells may be autologous.

"Autologous" refers to deriving from or originating in the same patient or individual. An "autologous transplant" refers to the harvesting and reinfusion or transplant of a subject's own cells or organs. Exclusive or supplemental use of autologous cells can eliminate or reduce many adverse effects of administration of the cells back to the host, particular graft versus host reaction.

In this case, the hematopoietic stem cells were collected from the said individual, genetically modified ex vivo or in vitro according to a method as described herein and administered to the same individual.

In a particular embodiment, the initial population of hematopoietic stem cells and/or blood cells may be derived from an allogeneic donor or from a plurality of allogeneic donors. The donors may be related or unrelated to each other, and in the transplant setting, related or unrelated to the recipient (or individual).

The stem cells to be modified as described herein may accordingly be exogenous to the individual in need of therapy.

In situations of administration of modified stem cells as described herein of exogenous origin, the said stem cells may be syngeneic, allogeneic, xenogeneic, or a mixture thereof.

"Syngeneic" refers to deriving from, originating in, or being members of the same species that are genetically identical, particularly with respect to antigens or immunological reactions. These include identical twins having matching MHC types. Thus, a "syngeneic transplant" refers to transfer of cells or organs from a donor to a recipient who is genetically identical to the donor.

"Allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

"Xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

Other embodiments of the invention utilizing endogenous hematopoietic stem cells involve the mobilization of the said stem cells from one anatomical niche of the individual to systemic circulation, or into another specific anatomical niche. Such mobilization is well known in the art and may for example be caused by administration of factors capable of stimulating stem cell exodus from compartments such as the bone marrow.

Where applicable, stem cells and progenitor cells may be mobilized from the bone marrow into the peripheral blood by prior administration of cytokines or drugs to the subject (see, e.g., Domingues et al. (Int. J. Hematol. 2017 feb; 105(2): 141-152)). Cytokines and chemokines capable of inducing mobilization include, by way of example and not limitation, granulocyte colony stimulating factor (G-CSF), granulocyte macrophage colony stimulating factor (GM-CSF), erythropoietin (Kiessinger, A. et al., Exp. Hematol. 23:609-612 (1995)), stem cell factor (SCF), AMD3100 (AnorMed, Vancouver, Canada), interleukin-8 (IL-8), and variants of these factors (e.g., pegfilgastrim, darbopoietin).

Cells prepared by a method as described herein may be resuspended in a pharmaceutically acceptable carrier and used directly or may be subjected to processing by various cell purification techniques available to the skilled artisan, such as FACS sorting, magnetic affinity separation, and immunoaffinity columns.

As already specified herein, the hematopoietic stem cells and blood cells as described herein are genetically modified in at least one of its globin gene, in particular in at least one of its endogenous globin gene.

Globin genes are organized in clusters in the genome of hematopoietic stem cells and blood cells, these clusters being called the α- and β-like human globin gene clusters.

The a-like human globin gene cluster comprises the zeta (ζ), pseudozeta (ψζ), mu (μ), pseudoalpha-1 (ψα1), pseudo-alpha-2 (ψα2), alpha 2 (α2), alpha 1 (α1) and theta (θ) globin genes and is located on the chromosome 16.

The β-like human globin gene cluster comprises the epsilon (ε), gamma-G (G γ), gamma-A (A γ), delta (δ) and beta (β) globin genes and is located on the chromosome 11.

Accordingly, the at least one globin gene comprised in the genome of a cell as described herein, and comprising the at least one transgene, can be in the α-like human globin gene cluster and/or in the β-like human globin gene cluster, in particular in the α-like human globin gene cluster or in the β-like human globin gene cluster.

In the present text, when the terms "a cell" without any more indication is mentioned, it applies to both an hematopoietic stem cell and to a blood cell as described herein.

According to an embodiment, the at least one globin gene as described herein is selected from the group consisting of the epsilon globin gene, the gamma G globin gene, the gamma A globin gene, the delta globin gene, the beta globin gene, the zeta globin gene, the pseudozeta globin gene, the mu globin gene, the pseudoalpha-1 globin gene, the alpha 1 globin gene and the alpha 2 globin gene.

In a particular embodiment, the at least one globin gene as described herein is selected from the group consisting of the gamma G globin gene, the gamma A globin gene, the delta globin gene, the beta globin gene, the alpha 1 globin gene and the alpha 2 globin gene, more particularly from the group consisting of the beta globin gene, the alpha 1 globin gene and the alpha 2 globin gene.

In a preferred embodiment, the at least one globin gene as described herein is selected from the group consisting of the alpha 1 globin gene and the alpha 2 globin gene.

The coding region of each globin gene is interrupted at two positions by stretches of noncoding DNA called intervening sequences (IVSs) or introns.

A globin gene is thus constituted, from its 5' end to its 3' end, of:
  a proximal promoter region;
  a 5' untranslated region (5' UTR);
  at least 2 exons, in particular 3 exons;
  at least 1 intron, in particular two introns; and/or
  a 3' untranslated region (3' UTR).

Accordingly, in a cell as described herein, the at least one transgene of interest comprised in the at least one globin gene of a cell as described herein can be comprised in the 5' region, in an exon, in an intron and/or in the 3'UTR of the said globin gene, in particular in the proximal promoter region, in the 5' UTR, in an exon and/or in an intron of the said globin gene.

Preferably, the at least one transgene of interest comprised in the at least one globin gene of a cell as described herein is comprised in the 5' region and/or in an intron of the said globin gene, in particular in the 5' UTR and/or in the proximal promoter and/or in an intron of the said globin gene, more particularly in the 5' UTR or in the proximal promoter or in an intron of the said globin gene.

In a particular embodiment, the at least one transgene of interest comprised in the at least one globin gene of a cell as described herein is comprised in the 5' region and/or in the second intron (IVS2) of the said at least one globin gene.

The 5' region according to the invention is the region upstream the translation initiation codon of the considered globin gene. It comprises the 5'UTR sequence of the gene and the proximal promoter.

In particular, the 5' region of a globin gene according to the invention corresponds to the 500 nucleotides sequence directly upstream said translation initiation codon of the considered globin gene, preferably the 400 nucleotides, more preferably the 300 nucleotides and more particularly the 250 nucleotides directly upstream said translation initiation codon of the considered globin gene.

In a particular embodiment, the 5' region of a globin gene according to the invention corresponds to the proximal promoter of the considered globin gene.

In another embodiment, the 5' region of a globin gene according to the invention corresponds to the 5'UTR (5' untranslated region) of the considered globin gene.

All the following positions are based on UCSC Genome Browser on Human December 2013 GRCh38/hg38 Assembly.

In particular, when considering the HBA1 (hemoglobin subunit alpha 1) human gene, the 5' region preferably corresponds to 5'UTR of this gene. This 5'UTR corresponds to the position chr16:176,651-176,716; 66 nt; RefSeq: NM_000558.4.

In particular, when considering the HBA2 (hemoglobin subunit alpha 2) human gene, the 5' region preferably corresponds to the 5'UTR of this gene. This 5'UTR corresponds to the position chr16:172,847-172,912; 66 nt; RefSeq: NM_000517.4.

When considering the HBB (hemoglobin subunit beta) human gene, the 5' region preferably corresponds to the proximal promoter of this gene. This proximal promoter corresponds to the position chr11:5,227,072-5,227,321 on UCSC Genome Browser on Human December 2013 GRCh38/hg38 Assembly.

More particularly, the at least one transgene of interest comprised in the at least one globin gene of a cell as described herein can be comprised in the 5' region, in the first intron (IVS1) and/or in the second intron (IVS2) of the said globin gene, preferably in the 5' UTR and/or in the proximal promoter and/or in the second intron (IVS2) of the said globin gene, more preferably in the 5' UTR and/or in the proximal promoter or in the second intron (IVS2) of the said globin gene.

When considering the HBA1 (hemoglobin subunit alpha 1) human gene, the first intron (IVS1) can correspond to the 117 nucleotides comprised between the first exon and the second exon of this gene. This region corresponds to the position chr16:176,812-176,928; 117 nt; RefSeq: NM_000558.4.

When considering the HBA2 (hemoglobin subunit alpha 2) human gene, the first intron (IVS1) can correspond to the 117 nucleotides comprised between the first exon and the second exon of this gene. This region corresponds to the position chr16:173,008-173,124; 117 nt; RefSeq: NM_000517.4.

When considering the HBB (hemoglobin subunit beta) human gene, the first intron (IVS1) can correspond to the 130 nucleotides comprised between the first exon and the second exon of this gene. This region corresponds to the position chr11:5,226,800-5,226,929; 130 nt; RefSeq: NM_000518.4.

When considering the HBA1 (hemoglobin subunit alpha 1) human gene, the second intron (IVS2) can correspond to the 149 nucleotides comprised between the second exon and the third exon of this gene. This region corresponds to the position chr16:177,134-177,282; 149 nt; RefSeq: NM_000558.4.

When considering the HBA2 (hemoglobin subunit alpha 2) human gene, the second intron (IVS2) can correspond to the 142 nucleotides comprised between the second exon and the third exon of this gene. This region corresponds to the position chr16:173,330-173,471; 142 nt; RefSeq: NM_000517.4.

When considering the HBB (hemoglobin subunit beta) human gene, the second intron (IVS2) can correspond to the 850 nucleotides comprised between the second exon and the third exon of this gene. This region corresponds to the position chr11:5,225,727-5,226,576; 850 NT; RefSeq: NM_000518.4.

The inventors indeed unexpectedly determined, as illustrated in the enclosed examples, that very good InDel percentages, defined further in the present text, as well as high transgene (GFP) expression are obtained when genome edition occurs in selected locations of the globin gene.

Accordingly, in a particular embodiment, a cell as described herein comprises in at least one of its globin gene comprised in the genome thereof, at least one transgene encoding at least one therapeutic protein or at least one therapeutic ribonucleic acid under the control of the endogenous promoter of the said at least one globin gene, the at least one globin gene being selected from the group consisting of the gamma G globin gene, the gamma A globin gene, the delta globin gene, the beta globin gene, the alpha 1 globin gene and the alpha 2 globin gene, more particularly from the group consisting of the beta globin gene, the alpha 1 globin gene and the alpha 2 globin gene, preferably from the group consisting of the alpha 1 globin gene and the alpha 2 globin gene; and the at least one transgene being comprised in the 5' region, in the first intron (IVS1) and/or in the second intron (IVS2) of the said globin gene, in particular in the 5' UTR and/or in the proximal promoter and/or in the second intron (IVS2) of the said globin gene, preferably in the 5' UTR or in the proximal promoter or in the second intron (IVS2) of the said globin gene.

In a particular embodiment, a cell as described herein comprises in at least one of its HBA globin gene comprised in the genome thereof, at least one transgene encoding at least one therapeutic protein or at least one therapeutic ribonucleic acid under the control of the endogenous promoter of the said at least one globin gene, the at least one transgene being comprised in the 5' region, in the first intron (IVS1) and/or in the second intron (IVS2) of the said globin gene, in particular in the 5' UTR and/or in the proximal promoter and/or in the second intron (IVS2) of the said globin gene, preferably in the 5' UTR or in the second intron (IVS2) of the said globin gene.

In a particular embodiment, a cell as described herein comprises in at least one of its HBB globin gene comprised in the genome thereof, at least one transgene encoding at least one therapeutic protein or at least one therapeutic ribonucleic acid under the control of the endogenous promoter of the said at least one globin gene, the at least one transgene being comprised in the 5' region, in the first intron (IVS1) and/or in the second intron (IVS2) of the said globin gene, in particular in the 5' UTR and/or in the proximal promoter and/or in the second intron (IVS2) of the said globin gene, preferably in the proximal promoter or in the second intron (IVS2) of the said globin gene.

According to a particular embodiment, a cell according to the invention is such that:

the at least one globin gene comprised in the genome of the said hematopoietic stem cell is alpha 1 globin gene and/or the alpha 2 globin gene and the at least one transgene encoding a therapeutic protein or a therapeutic ribonucleic acid is comprised in the 5' untranslated region (5'UTR) or in an intron, in particular is comprised in the 5' untranslated region (5'UTR) or in the second intron (IVS2), of the said at least one globin gene; and/or the at least one globin gene comprised in the genome of the said hematopoietic stem cell is the beta globin gene and the at least one transgene encoding a therapeutic protein or a therapeutic ribonucleic acid is comprised in the proximal promoter or in the second intron (IVS2) of the said at least one globin gene.

The present invention also relates to a blood cell, or erythroid cells, preferably purified, originating from a genetically modified stem cell as described herein.

The modified stem cell is in particular selected from the group consisting of an hematopoietic stem cell and an embryonic stem cell and is preferably an hematopoietic stem cell. In a preferred embodiment, a blood cell as described herein is a cell from the hematopoietic system.

Hematopoietic stem cell can differentiate into two types of progenitor cells, i.e. in myeloid progenitors or in lymphoid progenitors. While the myeloid progenitor will differentiate into megakaryocytes, thrombocytes, Erythrocytes, Mast cells, Myeloblasts, Basophils, Neutrophils, eosinophils, Monocytes and Macrophages, the lymphoid progenitor can differentiate into natural killer cells (NK), small lymphocytes, T lymphocytes, B lymphocytes and plasma cells.

Accordingly, a "blood cell" as described herein can be selected from the group consisting of lymphoid progenitors, myeloid progenitors, megakaryocytes, thrombocytes, erythrocytes, mast cells, myeloblasts, basophils, neutrophils, eosinophils, monocytes, macrophages, natural killer cells, small lymphocytes, T lymphocytes, B lymphocytes and plasma cells.

The hematopoietic stem cells and the lymphoid progenitors and myeloid progenitors will not express the transgene, but are still useful as they can differentiate into cells that are able to do so.

In a preferred embodiment, a blood cell as described herein is selected from the group consisting of megakaryocytes, thrombocytes, erythrocytes, mast cells, myeloblasts, basophils, neutrophils, eosinophils, monocytes, macrophages, natural killer cells, small lymphocytes, T lymphocytes, B lymphocytes and plasma cells.

Transgene

A transgene comprised in a cell as described herein encodes at least one protein and/or at least one ribonucleic acid, in particular encodes at least one therapeutic protein and/or at least one therapeutic ribonucleic acid, in particular encodes at least one therapeutic protein or at least one therapeutic ribonucleic acid.

The transgene of interest in a cell as described herein is under the control of the endogenous promoter of the globin gene comprising the said transgene.

In an embodiment, a cell as described herein can comprise only one transgene in one of its globin gene, the transgene encoding only one therapeutic protein or only one therapeutic ribonucleic acid as described herein.

In another embodiment, a cell as described herein can comprise only one transgene in one of its globin gene, the transgene encoding more than one therapeutic protein or more than one therapeutic ribonucleic acid as described herein, in particular two, three, four, five or six therapeutic proteins or therapeutic ribonucleic acids, preferably two therapeutic proteins or therapeutic ribonucleic acids.

When there is more than one therapeutic protein or therapeutic ribonucleic acid encoded by a transgene as described herein, the therapeutic proteins or therapeutic ribonucleic acids can be identical or different one from the other.

Moreover, when there is more than one transgene in a cell as described herein, the said transgenes can independently be in the same or in a different globin gene, and, if in the same globin gene, in the same or in a different part of the globin gene.

In another embodiment, a cell as described herein can comprise more than one transgene in at least one of its globin genes, in particular two, three, four, five or six transgenes.

According to this embodiment, the different transgenes can independently encode the same or different therapeutic protein(s) or therapeutic ribonucleic acid(s) from one transgene to another.

Also according to this embodiment, the different transgenes can independently encode one, or more than one, therapeutic protein(s) or therapeutic ribonucleic acid(s) as described herein.

In particular, all the transgenes can encode only one therapeutic protein or only one therapeutic ribonucleic acid. Alternatively, at least one, in particular all the transgenes can encode more than one, in particular two, three, four, five or six, more preferably two, therapeutic proteins or therapeutic ribonucleic acid.

Moreover, the therapeutic proteins or therapeutic ribonucleic acids encoded by the different transgenes can independently be identical or different.

Still according to this embodiment, the transgenes in a cell as described herein can independently be in the same or in a different globin gene, and, if in the same globin gene, in the same or in a different part of the globin gene.

In a particular embodiment, a therapeutic protein as described herein can naturally be secreted by the cell producing it or is engineered to be secreted.

For example, a therapeutic protein can be engineered by adding at least one signal peptide(s) to its sequence. A signal peptide is a short sequence present at the N-terminus of a peptide which is recognized by a cell and allows the translocation of the protein produced to the cellular membrane and its secretion.

According to another embodiment, a therapeutic protein according to the present text can be engineered by adding a short sequence that promotes its uptake by other cells or its crossing of the blood brain barrier or its binding to other proteins in the plasma or on endothelial cells.

A transgene as described herein can encode any type of therapeutic protein or therapeutic ribonucleic acid.

For example, a therapeutic protein encoded by a transgene comprised in a globin gene of a cell as described herein can be selected from the group consisting of cytokines, in particular interferon; hormones; chemokines; antibodies (including nanobodies); anti-angiogenic factors; or proteins for replacement therapy, such as for example enzymes and in particular alpha glucosidase, alpha-galactosidase and factor VIII.

In a particular embodiment, the transgene is different from the gene into which it is inserted.

According to a particular embodiment, a therapeutic protein encoded by a transgene comprised in a globin gene of a cell as described herein can be selected from the group consisting of growth factors, growth regulators, antibodies, antigens and their derivatives useful for immunization or vaccination. Such therapeutic proteins can in particular be selected from the group consisting of interleukins; insulin; G-CSF; GM-CSF; hPG-CSF; M-CSF; interferons, such as interferon-alpha, interferon-beta or interferon-pi; blood clotting factors such as Factor VIII, Factor IX or tPA; or combinations thereof. It is preferably selected from blood clotting factors and more particularly is Factor VIII.

Accordingly, in a particular embodiment, a therapeutic protein encoded by a transgene comprised in a globin gene of a cell as described herein can be selected from the group consisting of cytokines, in particular interferon (interferon-alpha, -beta or -gamma); hormones; chemokines; antibodies (including nanobodies); anti-angiogenic factors; enzymes for replacement therapy, such as for example adenosine deaminase, alpha glucosidase, alpha-galactosidase, idua and beta-glucosidase; interleukins; insulin; G-CSF; GM-CSF; hPG-CSF; M-CSF; blood clotting factors such as Factor VIII, Factor IX or tPA; transmembrane proteins such as Nerve Growth Factor Receptor (NGFR); lysosomal enzymes such as α-galactosidase (GLA), α-L-iduronidase (IDUA), lysosomal acid lipase (LAL) and galactosamine (N-acetyl)-6-sulfatase (GALNS); any protein that can be engineered to be secreted and eventually uptaken by disease affected cells (for example Lawlor M W, Hum Mol Genet. 22(8): 1525-1538. (2013); Puzzo F, Sci Transl Med. 29; 9(418) (2017); Bolhassani A. Peptides. 87:50-63., (2017))) and combinations thereof.

A therapeutic protein encoded by a transgene comprised in a globin gene of a cell as described herein is in particular a blood-clotting factor, and in particular factor VIII; or a lysosomal enzyme, such as lysosomal acid lipase (LAL) or galactosamine (N-acetyl)-6-sulfatase (GALNS).

A therapeutic protein encoded by a transgene comprised in a globin gene of a cell as described herein is more particularly a blood-clotting factor, and in particular factor VIII.

For example, a therapeutic ribonucleic acid encoded by a transgene comprised in a globin gene of a cell as described herein can be selected from the group consisting of miRNA, shRNA, siRNA, ncRNA and snRNA.

The protein encoding transgene can be in a wild-type form or a codon-optimized form, the latter being more particularly interesting when the non-optimized protein of interest is of great length. Such optimized sequences can advantageously allow higher transgene expression and protein production. Illustratively, a transgene encoding a human FVIII optimized transgene has been used in the examples of the present text.

The encoded protein can be any of the above proteins in a wild-type form or a codon-optimized form, the latter being more particularly interesting when the non-optimized protein of interest is of great length. Such optimized proteins can advantageously allow increasing the half-life and stability of the protein. Illustratively, a transgene encoding a human FVIII optimized protein has been used in the examples of the present text.

A therapeutic protein encoded by a transgene as described herein can also be a protein that can induce immune tolerance. Erythroid expression can indeed induce reactive T-cell deletion by inducing formation of regulatory T cells (Cremel et al. (Int. J. Pharm. 2013 Feb. 25:443(1-2): 39-49); Grimm et al. (Sci. Rep. 2015 Oct. 29; 5:15907) Kontos et al 5 (Proc. Natl. Acad. Sci. U.S.A. 2013 Jan. 2; 110(1):E60-8), an approach that can be therapeutically used to treat autoimmune diseases, such as diabetes type II and (Pishesha et al. Proc. Natl. Acad. Sci. U.S.A. 2017 Apr. 25; 114(17): E3583), or to avoid immune response against therapeutic proteins, such as GAA for Pompe disease and asparaginase (Lorentz et al. (Sci. Adv. 2015 Jul. 17; 1(6):e1500112); Cremel et al. (Int. J. Pharm. 2015 Aug. 1; 49(1-2):69-77)

In a particular embodiment, a transgene as described herein has a size inferior to 15 kb, more particularly inferior to 10 kb, preferably inferior to 8 kb.

Method for the Preparation of a Hematopoietic Stem Cell as Described Herein

A method for the preparation of a modified hematopoietic stem cell as described herein is in vivo, ex vivo or in vitro and is preferably ex vivo or in vitro.

The present invention in particular relates to a method for the ex vivo or in vitro preparation of an hematopoietic stem cell as described herein, the method comprising the steps of:
  (i) providing to the said stem cell a site-directed genetic engineering system by:
    (a) providing to the said stem cell (1) at least one guide nucleic acid binding to a selected target site or (2) a guide peptide-containing endonuclease binding to a selected target site, the said target site being located in a globin-encoding gene comprised in the genome of the said hematopoietic stem cell;
    (b) when the at least one guide nucleic acid has been provided at step a), further providing to the said stem cell at least one endonuclease devoid of target site specificity; and
    (c) further providing to the said stem cell a transgene that encodes at least one therapeutic protein or at least one therapeutic ribonucleic acid;
  and
  (ii) culturing the stem cell obtained at step (i) such that the said transgene is introduced at the said selected target site in the genome of the said hematopoietic stem cell.

A target site as described herein can be present in a domain of a globin gene as defined above, the said domain being selected from the group consisting of the 5' region, an exon domain, an intron domain and the 3'UTR domain of the globin gene, in particular from the group consisting of the 5' region, an exon domain and an intron domain of the said globin gene, more particularly from the group consisting of the 5' UTR, of the proximal promoter and an intron domain of the said globin gene.

In a preferred embodiment, the said target site is located in the 5' region and/or in an intron of the said at least one globin gene, preferably in the 5' untranslated region (5' UTR) and/or in the proximal promoter and/or in the second intron (IVS2) of the said at least one globin gene, in particular is comprised in the 5' untranslated region (5' UTR) or in the proximal promoter or in the second intron (IVS2) of the said at least one globin gene.

In a particular embodiment, step (i) (a) of a method as described herein is defined as providing to the said stem cell a guide peptide-containing endonuclease binding to a selected target site.

In another embodiment, step (i) (a) of a method as described herein is defined as providing to the said stem cell at least one guide nucleic acid (or gRNA) binding to a selected target site. gRNAs are target-specific short single-stranded RNA sequences with an 80 nucleotide constant region and a short 20 nucleotides target-specific sequence (in 5' of the gRNA sequence) that binds to a DNA target via Watson-Crick base pairing.

In a particular embodiment, step (i) (a) of a method as described herein is defined as providing to the said stem cell two guide nucleic acids (or gRNAs) binding to two different target sites in the same globin gene domain.

As defined above, step (i) (b) of a method as described herein is only present when step (i) (a) of the said method as described herein is defined as providing to the said stem cell at least one guide nucleic acid (or gRNA) binding to a selected target site.

An endonuclease as described herein is defined as being devoid of target site specificity, i.e. the said endonuclease is not able to recognize by itself a specific target site in the genome of the hematopoietic stem cell described herein.

In order to specifically cleave DNA at a particular target site, such endonuclease needs to be associated to a guide nucleic acid binding to the selected target site or to a guide peptide. When associated to a guide peptide, a guide peptide-containing endonuclease is mentioned herein.

When guided to the target site by the guide peptide or guide nucleic acid (gRNA), an endonuclease as described herein is able to introduce a single-stranded break or a double-stranded break in the said target site.

In particular, when a single guide nucleic acid molecule (gRNA) binding to a selected target site or a guide peptide-containing endonuclease binding to a selected target site is provided in step (i)(a) of the method as described herein, then the endonuclease part of the guide peptide-containing endonuclease or the endonuclease of step (i)(b) of the method as defined herein is able to introduce a double-stranded break at the target site.

In another embodiment, when two guide nucleic acid molecules (gRNAs) able to recognize two different target sites in the domain of the globin gene are provided in step (i)(a), one or two endonuclease(s) devoid of target site specificity can be provided in step (i)(b) of the method as described herein, the one or two endonuclease(s) being able to introduce a single-stranded break at the two different target sites.

Steps (i)(a), (i)(b) and (i)(c) of the method as described herein can be independently realized simultaneously or separately from one another. In a preferred embodiment, the at least one guide nucleic acid binding to a selected target site or the guide peptide-containing endonuclease binding to a selected target site of step (i)(a), the at least one endonuclease devoid of target site specificity of step (i)(b) and the transgene of step (i)(c) are provided simultaneously to the said stem cell.

Methods to introduce in vitro, ex vivo or in vivo proteins and nucleic acid molecules into cells are well known in the art. The traditional methods to introduce a nucleic acid, usually present in a vector, or a protein in a cell include microinjection, electroporation and sonoporation. Other techniques based on physical, mechanical and biochemical approaches such as magnetofection, optoinjection, optoporation, optical transfection and laserfection can also be mentioned (see Stewart M P et al., Nature, 2016).

In a particular embodiment, the endonuclease devoid of target site specificity of step (i)(b) is a RNA-guided endonuclease. In particular, this RNA-guided endonuclease can be directed by the gRNA to introduce a single- or a double-stranded break within at the target site.

A RNA-guided endonuclease as described herein can in particular be a Clustered regularly interspaced short palindromic repeats (CRISPR) associated protein (Cas), in particular the CRISPR associated protein 9 (Cas9) or the CRISPR-associated endonuclease in *Lachnospiraceae, Acidaminococcus, Prevotella* and *Francisella* 1 (Cpf1).

CRISPR-Cas systems for genome editing are particular systems using simple base pairing rules between an engineered RNA and the target DNA site instead of other systems using protein-DNA interactions for targeting.

CRISPR-Cas RNA-guided nucleases are derived from an adaptive immune system that evolved in bacteria to defend against invading plasmids and viruses.

According to a first embodiment, it consists in a mechanism by which short sequences of invading nucleic acids are incorporated into CRISPR loci. They are then transcribed and processed into CRISPR RNAs (crRNAs) which, together with a trans-activating crRNAs (tracrRNAs), complex with CRISPR-associated (Cas) proteins to dictate specificity of DNA cleavage by Cas nucleases through Watson-Crick base pairing between nucleic acids. The crRNA harbors a variable sequence known as the "protospacer" sequence. The protospacer-encoded portion of the crRNA directs Cas9 to cleave complementary target DNA sequences if they are adjacent to short sequences known as "protospacer adjacent motifs" (PAMs). Protospacer sequences incorporated into the CRISPR locus are not cleaved because they are not present next to a PAM sequence (see Mali et al. (Nat. Methods, 2013 October; 10(10):957-63); and Wright et al. (2016 Jan. 14; 164(1-2): 29-44 Cell).

According to this first embodiment, a guide RNA (gRNA) as described herein either corresponds to a single RNA (and is then called sgRNA) or corresponds to the fusion of the crRNA and tracrRNA. The term guide RNA or gRNA used in the present text designates these two forms, except when a particular form is specifically indicated.

In a gRNA according to this embodiment and corresponding to the fusion of the crRNA and tracrRNA, nucleotides 1-32 are the naturally-occurring crRNA while nucleotides 37-100 are the naturally-occurring tracrRNA, nucleotides 33-36 corresponding to a GAAA linker between the two pieces of gRNA (see Jinek et al. (2012) Science 337:816-821 and Cong et al. (2013) Science; 339(6121): 819-823).

Such gRNA is advantageously used in a CRISPR-Cas9 system.

gRNA are artificial and do not exist in nature.

Preferred gRNA as described herein can be selected among gRNA comprising a nucleic sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61 and SEQ ID NO: 63.

Particularly preferred gRNA as described herein can be selected among gRNA comprising a nucleic sequence selected from the group consisting of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61 and SEQ ID NO: 63, more preferably comprising a nucleic sequence selected from the group consisting of SEQ ID NO: 11, SEQ ID NO: 31 and SEQ ID NO: 37.

Preferred gRNA as described herein can be selected among gRNA consisting in a nucleic sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62 and SEQ ID NO: 64.

Particularly preferred gRNA as described herein can be selected among gRNA consisting in a nucleic sequence selected from the group consisting of SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62 and SEQ ID NO: 64, more preferably comprising a nucleic sequence selected from the group consisting of SEQ ID NO: 12, SEQ ID NO: 32 and SEQ ID NO: 38.

Other gRNAs, that can be used with different Cas or Cas9 nucleases having different PAMs, can be designed and used in a method according to the invention.

The said nucleic acid sequence of 20 nucleotides corresponds to the first 20 nucleotides at the 5' end of the gRNA sequence and, in the present first embodiment, directly precedes the PAM sequence, preferably the PAM sequence NGG, i.e. the sequences SEQ ID NO: 1-8 represents the nucleotides 1-20 of the gRNA sequence and the PAM signal is nucleotides 21-23.

In a PAM sequence, the N can be an adenine (A), a cytosine (C), a thymine (T) or a guanine (G).

As illustrated in the examples, among many designed gRNA targeting either the 5' region (5'UTR or proximal promoter) or the introns (IVS1 or IVS2) of HBA1/2 and HBB genes, the inventors selected specific gRNA for minimizing the possibility of generating an allele KO if the Cas9-induced Double Strain Break (DSB) doesn't result in a positive dDNA integration event.

According to another embodiment, the mechanism is similar to the one of the first embodiment mentioned above, except that no trans-activating crRNAs (tracrRNAs) is used. Indeed, in this embodiment, CRISPR RNAs (crRNAs) complex with CRISPR-associated (Cas) proteins to dictate specificity of DNA cleavage by Cas nucleases through Watson-Crick base pairing between nucleic acids. According to this embodiment, the Cas protein is advantageously Cpf1.

Indeed, an important difference between Cpf1 and Cas9 for example is that Cpf1 is a single-RNA-guided nuclease that does not require a tracrRNA.

The Cpf1 enzyme has been isolated from the bacteria *Francisella novicida*. The *Cpf*1 protein contains a predicted RuvC-like endonuclease domain that is distantly related to the respective nuclease domain of Cas9. However, Cpf1 differs from Cas9 in that it lacks HNH, a second endonuclease domain that is present within the RuvC-like domain of Cas9. Cpf1 recognizes a T-rich PAM, TTTN on the 5' side of the guide, which makes its distinct from Cas9 which uses a NGG PAM on the 3' side of the guide.

In the PAM sequence TTTN, the N can be an adenine (A), a cytosine (C), a thymine (T) or a guanine (G).

According to the present embodiment, a guide RNA (gRNA) as described herein corresponds to a sole crRNA and does not need to be fused with tracrRNA. Such gRNA is advantageously used in a CRISPR-Cpf1 system.

According to a particular embodiment, guide peptide-containing endonuclease binding to a selected target site of step (i)(a) of a method defined herein is a transcription activator-like effector nuclease (TALEN) or a zinc-finger nuclease.

The TALENs technology comprises a non-specific DNA-cleaving domain (nuclease) fused to a specific DNA-binding domain. The specific DNA-binding domain is composed of highly conserved repeats derived from transcription activator-like effectors (TALEs) which are proteins secreted by *Xanthomonas* bacteria to alter transcription of genes in host plant cells. The DNA-cleaving domain or cleavage half-domain can be obtained, for example, from various restriction endonucleases and/or homing endonucleases (for example Fok I Type IIS restriction endonuclease) of Fok I. (see Wright et al. (Biochem. J. 2014 Aug. 15; 462(1):15-24)).

The zinc-finger nuclease (ZFN) technology consists in the use of artificial restriction enzymes generated by fusion of a zinc finger DNA-binding domain to a DNA-cleavage domain (nuclease). The zinc finger domain specifically targets desired DNA sequences, which allows the associated nuclease to target a unique sequence within complex genomes.

The zinc finger DNA-binding domain comprises a chain of two-finger modules, each recognizing a unique hexamer (6 bp) sequence of DNA. The two-finger modules are stitched together to form a Zinc finger protein. As in the TALENs technology, the DNA-cleavage domain comprises the nuclease domain of Fok I (Carroll D, Genetics, 2011 August; 188(4): 773-782; Urnov F. D. Nat Rev Genet. (9):636-46, (2010)).

Concerning the transgene of step (i)(c) of the method as described herein, the said transgene is preferably not under the control of a promoter and/or that the provided transgene is under the control of a promoter that will not be inserted in the genome of the stem cell.

Indeed, as previously indicated, a genetically modified hematopoietic stem cell as described herein and that can be obtained from a method as defined previously is such that the at least one transgene comprised in a globin gene is under the control of the endogenous promoter of the said globin gene in which it is inserted.

The use of the endogenous promoter of a globin gene of a stem cell as described herein advantageously allows high and tissue specific transcription of the transgene(s) in the cell as mentioned above.

In step (ii) of a method as described herein, the stem cell obtained at step (i) is cultured such that the said transgene is introduced at the said selected target site in the genome of the said hematopoietic stem cell.

In a particular embodiment, the method for the ex vivo or in vitro preparation of an hematopoietic stem cell according as described herein comprises the steps of:
(i) providing to the said stem cell a site-directed genetic engineering system by:
  (a) providing to the said stem cell at least one guide nucleic acid binding to a selected target site, the said target site being located in a globin-encoding gene comprised in the genome of the said hematopoietic stem cell;
  (b) further providing to the said stem cell at least one endonuclease devoid of target site specificity; and
  (c) further providing to the said stem cell a transgene that encodes at least one therapeutic protein or at least one therapeutic ribonucleic acid;
  and
(ii) culturing the stem cell obtained at step (i) such that the said transgene is introduced at the said selected target site in the genome of the said hematopoietic stem cell.

As mentioned previously, the at least one globin gene is preferably selected from the group consisting of the epsilon globin gene, the gamma G globin gene, the gamma A globin gene, the delta globin gene, the beta globin gene, the zeta globin gene, the pseudozeta globin gene, the mu globin gene, the pseudoalpha-1 globin gene, the alpha 1 globin gene and the alpha 2 globin gene, in particular selected from the group consisting of the gamma G globin gene, the gamma A globin gene, the delta globin gene, the beta globin gene, the alpha 1 globin gene and the alpha 2 globin gene, more particularly selected from the group consisting of the alpha 1 globin gene and the alpha 2 globin gene.

In a particular embodiment, the present invention relates to method for the in vivo, ex vivo or in vitro preparation, in particular ex vivo or in vitro preparation, of an hematopoietic stem cell according to any one of claims 1 to 5, comprising the steps of:
(i) providing to the said stem cell a site-directed genetic engineering system by:
  (a) providing to the said stem cell at least one guide nucleic acid binding to a selected target site, the said target site being located in the 5' region and/or in the second intron (IVS2) of an endogenous globin-encoding gene comprised in the genome of the said hematopoietic stem cell;
  (b) further providing to the said stem cell at least one Clustered regularly interspaced short palindromic repeats (CRISPR) associated nuclease, in particular the CRISPR associated protein 9 (Cas9); and
  (c) further providing to the said stem cell a transgene that encodes at least one therapeutic protein or at least one therapeutic ribonucleic acid;
  and
(ii) culturing the stem cell obtained at the end of step (i) such that the said transgene is introduced at the said selected target site in the genome of the said hematopoietic stem cell.

In a particular embodiment, the present invention relates to method for the in vivo, ex vivo or in vitro preparation, in particular ex vivo or in vitro preparation, of an hematopoietic stem cell according to any one of claims 1 to 5, comprising the steps of:
(i) providing to the said stem cell a site-directed genetic engineering system by:
  (a) providing to the said stem cell at least one guide nucleic acid binding to a selected target site, the said target site being located in the 5' region and/or in the second intron (IVS2) of an endogenous globin-encoding gene comprised in the genome of the said hematopoietic stem cell;
  (b) further providing to the said stem cell at least one Clustered regularly interspaced short palindromic repeats (CRISPR) associated nuclease, in particular the CRISPR associated protein 9 (Cas9); and
  (c) further providing to the said stem cell a transgene that encodes at least one therapeutic protein or at least one therapeutic ribonucleic acid;
  and
(ii) culturing the stem cell obtained at the end of step (i) such that the said transgene is introduced at the said selected target site in the genome of the said hematopoietic stem cell,
the said at least one guide nucleic acid binding to a selected target site being selected from the group consisting of gRNAs consisting in a nucleic sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62 and SEQ ID NO: 64, preferably comprising a nucleic sequence selected from the group consisting of SEQ ID NO: 12, SEQ ID NO: 32 and SEQ ID NO: 38.

Pharmaceutical Composition

As already described elsewhere in the present specification, the present invention also relates to a pharmaceutical composition comprising at least one genetically modified hematopoietic stem cell as described herein and/or at least one blood cell (or erythroid cell) as described herein in a pharmaceutically acceptable medium.

A pharmaceutically acceptable medium as described herein is in particular suitable for administration to a mammalian individual.

A "pharmaceutically acceptable medium" comprises any of standard pharmaceutically accepted mediums known to those of ordinary skill in the art in formulating pharmaceutical compositions, for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxym ethyl cellulose, hydroxylpropyl methyl cellulose, magnesium stearate, calcium phosphate, gelatine or polysorbate 80 or the like.

A pharmaceutical composition as described herein will often further comprise one or more buffers (e.g., neutral buffered saline or phosphate buffered saline); carbohydrates (e.g., glucose, mannose, sucrose or dextrans); mannitol; proteins; polypeptides or amino acids such as glycine; antioxidants (e.g., ascorbic acid, sodium metabisulfite, butylated hydroxytoluene, butylated hydroxyanisole, etc.); bacteriostats; chelating agents such as EDTA or glutathione; solutes that render the formulation isotonic, hypotonic or weakly hypertonic with the blood of a recipient; suspending agents; thickening agents and/or preservatives.

Of course, the type of carrier will typically vary depending on the mode of administration.

In an embodiment, the cells as described herein can be used in a composition in combination with therapeutic compounds that are effective in treating the conditions associated with the disorder/disease to be treated in the individual in need thereof. For example, a cell as described herein can be administered with antibacterial, antifungal, or antiviral compounds for preventing opportunistic infections or infections already in progress in the individual. Illustratively, platelets can be administered together with cells as described herein in a composition as described herein as a temporary measure to restore platelet count to safe levels.

In an embodiment, the cells as described herein can be used in a composition as described herein in combination with other hematopoietic stem cells or blood cells as defined above, but not modified as described herein.

In an embodiment, the cells as described herein can be used in a composition as described herein in combination with other agents and compounds that enhance the therapeutic effect of the administered cells.

In another embodiment, the cells as described herein can be administered in a composition as described herein with therapeutic compounds that augment the differentiation of the hematopoietic stem cell or progenitor cells as described herein. These therapeutic compounds have the effect of inducing differentiation and mobilization of hematopoietic stem cells and/or of progenitor cells that are endogenous, and/or the ones that are administered to the individual as part of the therapy.

Genetically Modified Cells for their Use as a Medicament

Another object of the present invention is a hematopoietic stem cell as described herein, or a blood cell as described herein, or a pharmaceutical composition as described herein, for its use as a medicament.

Cells as described herein are administered into a subject by any suitable route, such as intravenous, intracardiac, intrathecal, intramuscular, intra-articular or intra-bone marrow injection, and in a sufficient amount to provide a therapeutic benefit.

The amount of the cells needed for achieving a therapeutic effect will be determined empirically in accordance with conventional procedures for the particular purpose.

Generally, for administering the cells for therapeutic purposes, the cells are given at a pharmacologically effective dose.

By "pharmacologically effective amount" or "pharmacologically effective dose" is meant an amount sufficient to produce the desired physiological effect or amount capable of achieving the desired result, particularly for treating the disorder or disease condition, including reducing or eliminating one or more symptoms or manifestations of the disorder or disease.

Illustratively, administration of cells to a patient suffering from a neutropenia provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

Cells are administered by methods well known in the art. In one embodiment, the administration is by intravenous infusion. In another method, the administration is by intra-bone marrow injection.

The number of cells transfused will take into consideration factors such as sex, age, weight, the types of disease or disorder, stage of the disorder, the percentage of the desired cells in the cell population (e.g., purity of cell population), and the cell number needed to produce a therapeutic benefit.

Generally, the numbers of cells infused may be from $1.10^4$ to $5.10^6$ cells/kg, in particular from $1.10^5$ to $10.10^6$ cells/kg, preferably from $5.10^5$ cells to about $5.10^6$ cells/kg of body weight.

A pharmaceutical composition as described herein, as previously mentioned, can be used for administration of the cells as described herein into the individual in need thereof.

The administration of cells can be through a single administration or successive administrations. When successive administrations are involved, different cells numbers and/or different cells populations may be used for each administration.

Illustratively, a first administration can be of a cell or a cell population as described herein that provides an immediate therapeutic benefit as well as more prolonged effect (erythrocytes and/or Common Myeloid Progenitor cells (CMP) and/or hematopoietic stem cell (HSC)+granulocyte/macrophage progenitor cells (GMP)+neutrophils) while the second administration includes cells as described herein that provide prolonged effect (e.g., CMP and/or HSC) to extend the therapeutic effect of the first administration.

A stem cell, a blood cell or a pharmaceutical composition as described herein can be used in the treatment of:
 a disease selected from the group consisting of autoimmune diseases, viral infections and tumors; and/or
 a disease caused by the lack of a protein or by the presence of an aberrant non-functional protein in an individual in need thereof.

Accordingly, a further object of the invention is a genetically modified hematopoietic stem cell as described herein, or a blood cell as described herein, or a pharmaceutical composition as described herein, for its use in the treatment of:
 a disease selected from the group consisting of autoimmune diseases, viral infections and tumors; and/or
 a disease caused by the lack of a protein or by the presence of an aberrant non-functional protein,
 in an individual in need thereof.

It can also be mentioned a method for the treatment of:
 a disease selected from the group consisting of autoimmune diseases, viral infections and tumors; and/or
 a disease caused by the lack of a protein or by the presence of an aberrant non-functional protein,
 in an individual in need thereof,
comprising the administration of an hematopoietic stem cell as described herein, a blood cell of the invention, and/or a pharmaceutical composition as described herein to said individual in need thereof.

The present invention also relates to the use of an hematopoietic stem cell as described herein, a blood cell of the invention, and/or a pharmaceutical composition as described herein for the manufacture of a medicament for treating:
 a disease selected from the group consisting of autoimmune diseases, viral infections and tumors; and/or
 a disease caused by the lack of a protein or by the presence of an aberrant non-functional protein,
 in an individual in need thereof.

In a particular embodiment, a stem cell, a blood cell or a pharmaceutical composition as described herein can be used in the treatment of a disease caused by the lack of a secreted protein or by the presence of an aberrant non-functional secreted protein in an individual in need thereof.

Such disease can for example be selected from the group consisting a coagulation disorder, a lysosomal storage disorder, an hormonal defect and an alpha-1 antitrypsin deficiency.

Lysosomal storage disorders can for example be selected from Gaucher's disease (glucocerebrosidase deficiency-gene name: GBA), Fabry's disease (a galactosidase deficiency-GLA), Hunter's disease (iduronate-2-sulfatase deficiency-IDS), Hurler's disease (alpha-L iduronidase deficiency-IDUA), and Niemann-Pick's disease (sphingomyelin phosphodiesterase 1 deficiency SMPD1).

In another embodiment, a stem cell, a blood cell or a pharmaceutical composition as described herein can be used in the treatment of a disease selected from the group consisting of autoimmune diseases, viral infections and tumors.

Indeed, according to an embodiment of the invention, the therapeutic protein of the invention can be a therapeutic antibody that can be used for neutralization of target proteins, like bacterio-toxins, or proteins that directly cause disease (e.g. VEGF in macular degeneration) as well as highly selective killing of cells whose persistence and replication endanger the host (e.g. cancer cells, as well as certain immune cells in autoimmune diseases).

The present invention further relates to a genetically modified hematopoietic stem cell as described herein, or a blood cell as described herein, or a pharmaceutical composition as described herein, for its use in inducing immune tolerance to an individual in need thereof.

The present invention is further illustrated by, without in any way being limited to, the examples herein.

EXAMPLES

Example 1: Design and Validation of gRNAs in K562 Erythroleukemia Cell Line

As previously indicated, the inventors designed several gRNA targeting the 5' region (5' UTR or proximal promoter) or one of the introns (IVS1 or IVS2) of HBA1/2 or HBB genes.

gRNA candidates encoding plasmids were nucleofected in a stable K562 cell clone constitutively expressing SpCas9 (K562-Cas9).

The gRNA candidates used in this example are those having the following sequences:

For HBA, from left to right: SEQ ID NO: 4, 6, 8, 12, 14, 16, 18, 20, 22, 24, 26, 28, 30, 32, 34, 36 and 38; For HBB, from left to right: SEQ ID NO: 40, 42, 44, 46, 48, 50, 52, 54, 56, 58, 60, 62 and 64.

More particularly, K562 (ATCC® CCL-243) were maintained in RPMI 1640 medium (Gibco) containing 2 mM glutamine and supplemented with 10% fetal bovine serum (FBS, BioWhittaker, Lonza), HEPES (10 mM, LifeTechnologies), sodium pyruvate (1 mM, LifeTechnologies) and penicillin and streptomycin (100 U/ml each, LifeTechnologies). A stable clone of K562-Cas9 was made by infection with a lentiviral vector (Addgene #52962) expressing spCas9 and a blasticidin resistance cassette, selected and subcloned.

$2.5 \times 10^5$ of K562-Cas9 cells were transfected with 200 ng of gRNA-containing vector (Addgene #53188) in a 20 gL volume using Nucleofector Amaxa 4D (Lonza) with SF Cell Line 4D-Nucleofectof Kit.

48 hours after nucleofection, cells were pelleted, and DNA was extracted using MagNA Pure 96 DNA and Viral NA Small Volume Kit (Roche). 50 ng of genomic DNA were used to amplify the region that spans the cutting site of each gRNA using KAPA2G Fast ReadyMix (Kapa Biosystem). After Sanger sequencing, the percentage of Inversions and Deletions (InDel) was calculated by the software TIDE (Tracking of InDels by Decomposition—Brinkman et al. Nucleic Acids Res. 2014. 42(22):e168)) using the website www.tide.calculator.nk.

The InDel is the insertion or deletion of bases in the genome caused by non-homologous end joining (NHEJ) DNA repair of the DNA ends generated by the nuclease activity. It is well defined in Brinkman et al. (Brinkman et al. Nucleic Acids Res. 2014. 42(22):e168)). Accordingly, the closer to 100% an InDel result, the more efficient the gRNA tested.

The best performing gRNA for target locus 5' region, in particular the 5'UTR, IVS1 and IVS2 of HBA (respectively the gRNA having the sequence SEQ ID NO: 12 for 5' region, the gRNA having the sequence SEQ ID NO: 32 for IVS1 and the gRNA having the sequence SEQ ID NO: 38 for IVS2) were further tested for integration and expression of transgene containing donor DNA (dDNA). As dDNA, integrase-defective lentiviral vectors (IDLV) encoding for a promoter-less GFP were generated, expected to be under the control of the endogenous α/β globin promoter upon successful targeting, and a puromycin expression cassette, to enrich for dDNA containing cells.

To test dDNA integration, K562-Cas9 cells were first transduced with Integrase-Deficient Lentiviral Vectors (IDLV) and 24 h later transfected with the selected gRNA-encoding plasmids. After puromycin selection, a high percentage of GFP positive cells were observed for all gRNA and dDNA tested (data not shown) while no significant GFP expression was detected upon random integration of the cassette (not shown).

The inventors then induced erythroid differentiation of K562 to upregulate HBA and HBB transcription and observed a concomitant increase in GFP expression, confirming that the reporter was indeed under the transcriptional regulation of endogenous globin promoters (data not shown). Finally, correct integration for all gRNA/dDNA combinations was validated by PCR and Sanger sequencing on single GFP+ cell clones (data not shown).

In summary, the inventors identified several efficient gRNA and designed dDNA cassettes to achieve precise and functional transgene targeted integration under the control of the endogenous erythroid α and β-globin promoters.

Example 2: Targeted Integration in HBA and HBB Locus of a Transgene Enables Endogenous Promoter Regulation of the Said Transgene The inventors confirmed that a transgene inserted in a globin locus is under the control of the endogenous promoter of the corresponding globin gene.

Accordingly, K562 cells transfected in order to insert a GFP gene in various domains of their HBA or HBB gene underwent erythroid differentiation upon induction with hemin on the basis of the protocol indicated hereafter. The said differentiation led to an upregulate of HBA or HBB transcripts and GFP expression was monitored and compared in non-differentiated (GPA−) and differentiated cells (GPA+).

$5 \times 10^5$ of K562-Cas9 cells were transduced with IDLV containing a promoterless GFP and a constitutively expressed Puromycin-resistance gene.

The traps were designed to be expressed upon integration in the HBA or HBB 5' region (5'UTR for HBA, proximal promoter for HBB) or introns. The day after transduction, cells were washed and $2.5 \times 10^5$ of transduced cells were transfected with 200 ng of gRNA-containing vector using NucleofectorAmaxa 4D (Lonza) with SF Cell Line 4D-Nucleofector Kit.

Two weeks later, cells were selected with puromycin (5 ug/ml) to enrich for IDLV integration and GFP positive cells were sorted using MoFlocell sorter (Beckman Coulter). GFP positive cells for each combination of gRNA/IDLV were differentiated for 4 days by adding hemin to medium (50 uM). As K562 differentiation is not homogeneous, in order to determine differentiation status, cells were stained with an anti Glycophorin A (GPA or GYPA) antibody (PECy7 Mouse Anti-Human CD235a, CLONE GA-R2, BD Bioscience) and GFP expression was analyzed by flow cytometry.

The results obtained (see FIG. 2) show an increase in GFP expression upon erythroid induction in targeted cells but not in the control cells (IDLV integrated in the AAVS1 locus (gRNA AAVS1) or randomly (gRNA Luc)).

These results illustrate the fact that the reporter transgene is indeed under the control of the transcriptional regulation of endogenous globin promoters.

Example 3: Targeted Integration of a Donor DNA in HBA Allows Stable Expression of Different Transgenes The inventors confirmed that different transgenes can be successfully inserted in a globin locus under the control of the endogenous promoter of the corresponding globin gene according to the invention.

$5 \times 10^5$ of K562-Cas9 cells were transduced with Integrase-Deficient lentiviral vectors (IDLV) containing a promoterless truncated nerve growth factor receptor (DNGFR) or a codon-optimized Factor VIII (F8) and a constitutively expressed Puromycin-resistance gene. The traps were designed to be expressed upon on target integration. The day after transduction cells were washed and $2.5 \times 10^5$ of transduced cells were transfected with 200 ng of HBA 5'UTR gRNA-containing vector using NucleofectorAmaxa 4D (Lonza) with SF Cell Line 4D-Nucleofector Kit.

2 weeks later cells were selected with puromycin (5 ug/ml) to enrich for IDLV integration.

The results obtained are represented in FIG. 3.

Left Panel: Puromycin-selected cells were stained with anti-NGFR (mouse anti human CD271-APC, Miltenyi Biotec) and analysed by flow cytometry.

Right Panel: a representative clone of puromycin-selected cells that integrated the F8-Puromycin trap in HBA.

Cells were fixed and permeabilized using Cytofix/Cytoperm™ (BD Bioscience) and F8 expression was monitored by flow cytometry (Mouse anti human FVIII GMA-8015, Green Mountain and Goat anti-Mouse IgG (H+L) Alexa Fluor 488, Invitrogen).

The inventors demonstrated that the method according to the invention allows the induction of a stable expression of different transgenes in globin genes of cells of interest.

Example 4: Effect of Homology Arms on Target Integration Efficiency in Hematopoietic Stem/Progenitor Cells The effect of the addition of homology arms to the donor DNA trap was observed.

Mobilized peripheral blood HSPC were thawed and cultured in prestimulation media for 48 h (StemSpan, Stem Cell technologies; rhSCF 300 ng/ml, Flt3-L 300 ng/ml, rhTPO 100 ng/ml and IL-3 20 ng/mL, CellGenix).

Specific crRNA and scaffold tracrRNA (Integrated DNA Technologies) for gRNA 5'UTR were annealed following manufacturer's instruction and ribonucleoprotein complexes were formed with 30 pmol of spCas9 (ratio 1:1.5). $2 \times 10^5$ cells per condition were nucleofected with RNP complex using P3 Primary Cell 4D-Nucleofector kit (Lonza) and transduced with a GFP-Puromycin vector trap with or without homology arms for 5'UTR gRNA target site (250 bp on each side of the transgene).

The traps were provided as IDLV (no homology, MOI 100, top panel) or AAV6 vectors (homology arms, MOI 15000, lower panel). After transduction cells were washed and left in pre-stimulation media for additional 48 hours in the presence of StemregeninI (0.75 uM, Stem Cell Technologies) and Z-VAD pan caspase inhibitor (120 uM, InvivoGen) and cultured for 14 days in erythroid differentiation medium (StemSpan, Stem Cell Technologies; SCF 20 ng/ml, Epo 1 u/mL, IL3 5 ng/ml, Dexamethasone 2 µM and Betaestradiol 1 µM).

GFP expression was monitored along erythroid differentiation by flow cytometry.

The results obtained are represented in FIG. 4.

It can be seen that target integration efficiency dramatically increases with the addition of homology arms to the donor DNA trap delivered by AAV.

Example 5: Effect of On-Target Activity of Each gRNA on HBA Production in K562

To evaluate if Cas9/gRNA induced DNA double strand brake can affect HBA expression in absence of donor DNA integration, we transfected candidate gRNA in Cas9-K562 and we monitored the expression of HBA by western blot or HbF (Foetal Hemoglobin, composed of 2 HBA and 2 HBG chain) by FACS.

Firstly, $2.5 \times 10^5$ of K562-Cas9 cells were transfected with 200 ng of gRNA-containing vector using NucleofectorAmaxa 4D (Lonza) with SF Cell Line 4D-Nucleofector Kit. Genome editing efficiency was measured by TIDE analysis on PCR products.

A week after nucleofection, cells were fixed and permeabilized using Cytofix/Cytoperm™ (BD Bioscience) and HbF expression was monitored by flow cytometry (APC Mouse Anti-Human Fetal Hemoglobin CLONE 2D12, BD Bioscience).

The results obtained are represented in the top part of FIG. 5.

Genome editing efficiencies at specific sites of the HBA genes are indicated on top of each histograms as percentage of edited alleles (InDel).

Moreover, a million of nucleofected cells were lysed in RIPA buffer (50 mM Tris-HCl pH 7.4, 150 mM NaCl, 1% Triton x-100, 1% Sodium deoxycholate, 0.1% SDS) supplemented with Complete™, Protease Inhibitor Cocktail (Roche).

Cell lysates were quantified by BCA Protein Assay (Thermofisher). Samples were denatured for 5 minutes at 90° C. in presence of 1× reducing agent and sample loading dye (Invitrogen). 30 ug of total protein was run in MES 1× (Invitrogen) at 200V using Bolt Bis-Tris 4-12% Plus Gel (Invitrogen); proteins were transferred in a nitrocellulose membrane by IBlot2 system (Invitrogen). After blocking for 2 h with Odyssey TBS Blocking buffer (Li-Cor), membranes were incubated with primary antibodies against alpha globin (goat anti Hemoglobin a Antibody D-16, Santa Cruz) and β-Tubulin (Rabbit Polyclonal Antibody, Li-Cor) and washed in TBS-0.1% Tween20. Specie-specific secondary antibodies were used 1:10000 (Donkey anti Goat IrDye 800 and Mouse anti-rabbit IrDye 680, Li-Cor). Data were acquired with Odyssey Infrared Imaging System and analyzed with Image Studio Lite.

The results obtained are represented in the medium part of FIG. 5.

Genome editing efficiencies at specific sites of the HBA genes are indicated below the lanes as percentage of edited alleles (InDel).

Although we obtained high level of gRNA induced genomic double strand breaks (InDel percentage), no effect on HBB or HbF expression was detected, indicating that Cas9 induced DSB does not affect/reduce endogenous expression of alpha-globin chain.

In this example, the gRNA used are the following:
for 5'UTR, the gRNA having the sequence SEQ ID NO: 12;
for KO, the gRNA having the sequence SEQ ID NO: 14;
for IVS1, the gRNA having the sequence SEQ ID NO: 32; and
for IVS2, the gRNA having the sequence SEQ ID NO: 38.
UT are control cells (not transfected).

Moreover, mobilized peripheral blood HSPC were thawed and cultured in prestimulation media for 48 h (StemSpan, Stem Cell technologies; rhSCF 300 ng/ml, Flt3-L 300 ng/ml, rhTPO 100 ng/ml and IL-3 20 ng/mL, CellGenix). Specific crRNA and scaffold tracrRNA (Integrated DNA Technologies) were annealed following manufacturer's instruction and ribonucleoprotein complexes were formed with 30 pmol of spCas9 (ratio 1:1.5). $2 \times 10^5$ cell per condition were nucleofected with RNP complex using P3 Primary Cell 4D-Nucleofector kit (Lonza) and cultured for 14 days in erythroid differentiation medium (StemSpan, Stem Cell Technologies; SCF 20 ng/ml, Epo 1 g/mL, IL3 5 ng/ml, Dexamethasone 2 µM and Betaestradiol 1 µM). Cells were fixed and permeabilized using Cytofix/Cytoperm™ (BD Bioscience) and HbF expression was monitored by flow cytometry (APC Mouse Anti-Human Fetal Hemoglobin CLONE 2D12).

The results obtained are represented in the bottom part of FIG. 5.

Genome editing efficiencies at specific sites of the HBA genes are indicated above the graphs as percentage of edited alleles (InDel).

Here too, although we obtained high level of gRNA induced genomic double strand breaks (InDel percentage), no effect on HBB or HbF expression was detected, indicating that DSB induced by our HBA gRNA candidates do not affect/reduce endogenous expression of alpha-globin chain in human HSPC-derived erythroid cells.

Example 6: Targeted Sites of Integration of the Invention do not Severely Affect HBA or HBB Synthesis in HSPC-Derived Erythroblasts Mobilized peripheral blood HSPC have been nucleofected with gRNA targeting different specific sites (5' UTR, second intron (IVS2) or first exon (KO)) in the HBA or HBB genes and differentiated towards the erythroid lineage to activate globin expression.

The gRNA used to target the first exon in HBB (HBB KO) has the partial sequence CTTGCCCCACAGGGCAGTAA (SEQ ID NO: 65) and the full sequence CTTGCCCCACAGGGCAGTAACGG (SEQ ID NO: 66).

The gRNA used to target the AAVS1 gene (AAVS1) has the partial sequence GTCCCCTCCACCCCACAGTG (SEQ ID NO: 67) and the full sequence GTCCCCTCCACCCCACAGTGGGG (SEQ ID NO: 68).

The gRNA used to target the first exon in HBA1/2 (HBA KO) is the one named HBA 16.1, having the partial sequence GTCGGCAGGAGACAGCACCA (SEQ ID NO: 13) and the full sequence GTCGGCAGGAGACAGCACCATGG (SEQ ID NO: 14)

In particular, mobilized peripheral blood HSPC have been thawed and cultured in prestimulation media for 48 h (StemSpan, Stem Cell technologies; rhSCF 300 ng/ml, Flt3-L 300 ng/ml, rhTPO 100 ng/ml and IL-3 20 ng/mL, CellGenix). Specific crRNA and scaffold tracrRNA (Integrated DNA Technologies) were annealed following manufacturer's instruction and ribonucleoprotein complexes were formed with 30 pmol of spCas9 (ratio 1:1.5).

$2.10^5$ cells per condition were nucleofected with Cas9 ribonucleoprotein (RNP) complex using P3 Primary Cell 4D-Nucleofector kit (Lonza) and cultured for 14 days in erythroid differentiation medium (StemSpan, Stem Cell Technologies; SCF 20 ng/ml, Epo 1 g/mL, IL3 5 ng/ml, Dexamethasone 2 µM and Betaestradiol 1 µM) or in semi-solid Methocult medium (H4435, StemCell Technologies) for 14 days for colony-forming cells (CFC) assay.

The differentiated HSPC-derived erythroblasts were then lysed in water and the hemoglobin subunits content was measured by chromatography.

High performance liquid chromatography (HPLC) analysis was performed using a NexeraX2 SIL-30AC chromatograph (Shimadzu, Kyoto, Japan) and analyzed with LC Solution software.

Globin chains were separated using a 250×4.6 mm, 3.6 µm Aeris Widepore column (Phenomenex). The samples were eluted with a gradient mixture of solution A (water/acetonitrile/trifluoroacetic acid, 95:5:0.1) and solution B (water/acetonitrile/trifluoroacetic acid, 5:95:0.1), monitoring absorbance at 220 nm.

The results obtained are represented in FIG. 6.

Using RNP nucleofection, the inventors demonstrated that editing the specific regions of HBA and HBB considered in the present invention does not significantly alter HBA or HBB synthesis in HSPC-derived erythroblasts, as assessed by HPLC quantification of hemoglobin subunits in both liquid culture and red colonies. Major changes were instead observed when the coding sequences of these genes were targeted (HBA KO and HBB KO controls).

Example 7: Targeted Integration of a Donor DNA in HBA Allows Stable Expression of FVIII or FIX Transgenes Different transgenes were integrated in the HBA gene and functional clotting factors exploiting the transcriptional control of the endogenous α-globin promoter were secreted.

Experimentally, K562-Cas9 cells were transduced with an IDLV containing a promoterless FIX or codon-optimized Factor VIII (F8) transgenes. These IDLV were designed to be expressed upon target integration.

After 24 hours, cells were transfected with a gRNA expressing plasmid to generate a double-stranded break at the 5'UTR of the HBA locus. Single-cell clones with monoallelic on-target integration of FVIII or FIX cassette were selected to measure the activity of secreted FVIII and FIX in cell supernatants by activated partial thromboplastin time (aPTT) assay.

Similar measurements were made with supernatants from untransduced cells as control (CTRL).

The results obtained are represented in FIG. 7.

This invention allows the stable expression of different transgenes, in the present case FVIJ and FIX, upon targeted integration in globin genes of cells of interest.

Sequences Table

| | Partial sequence | SEQ ID NO | Full Sequence | SEQ ID NO |
|---|---|---|---|---|
| HBA gRNA name | | | | |
| HBA 4 | GGGGCGCGGCCTGGACCGCA | 1 | GGGGCGCGGCCTGGACCGCAGGG | 2 |
| HBA 10 | GGGTTTATGCTTGGGGCGCG | 3 | GGGTTTATGCTTGGGGCGCGGGG | 4 |
| HBA 12 | GACTCAGAGAGAACCCACCA | 5 | GACTCAGAGAGAACCCACCATGG | 6 |
| HBA 14 | TGGGTTCTCTCTGAGTCTGT | 7 | TGGGTTCTCTCTGAGTCTGTGGG | 8 |
| HBA 19.1 | GCGCGGGGCACGCCCGGCC | 9 | GCGCGGGGCACGCCCGGCCGGG | 10 |
| HBA 15.1 | GGGTTCTCTCTGAGTCTGTG | 11 | GGGTTCTCTCTGAGTCTGTGGGG | 12 |
| HBA 16.1 | GTCGGCAGGAGACAGCACCA | 13 | GTCGGCAGGAGACAGCACCATGG | 14 |
| HBA 17-G | GCAGGAGACAGCACCATGGT | 15 | GCAGGAGACAGCACCATGGTGGG | 16 |
| HBA 20.1 | CATAAACCCTGGCGCGCTCG | 17 | CATAAACCCTGGCGCGCTCGCGG | 18 |
| HBA 5.1 | TTGAATGCTCCAGCCGGTTC | 19 | TTGAATGCTCCAGCCGGTTCCAG | 20 |
| gRNA2 | CGGGAGGCTTCGCCCAATCC | 21 | CGGGAGGCTTCGCCCAATCCTGG | 22 |
| gRNA3 | CGGGCGAGCGAGTGCGAGCC | 23 | CGGGCGAGCGAGTGCGAGCCGG | 24 |
| gRNA11 | GGGGAGGCTTCGCCCAATCCT | 25 | GGGGAGGCTTCGCCCAATCCTGGG | 26 |
| HBA INT1 72.1 | CAGGCCACCCTCAACCGTCC | 27 | CAGGCCACCCTCAACCGTCCTGG | 28 |
| HBA INT1 73.2 | TCCGGGGCCAGGACGGTTGA | 29 | TCCGGGGCCAGGACGGTTGAGGG | 30 |
| HBA INT1 73b.1 | GTCCGGGGCCAGGACGGTTG | 31 | GTCCGGGGCCAGGACGGTTGAGG | 32 |
| HBA INT2 13.2 | CCCTCGACCCAGATCGCTCC | 33 | CCCTCGACCCAGATCGCTCCCGG | 34 |
| HBA INT2 63.2 | GAAGAGGGTCAGTGCGGCCC | 35 | GAAGAGGGTCAGTGCGGCCCAGG | 36 |
| HBA INT2 74.1 | GCGTGATCCTCTGCCCTGAG | 37 | GCGTGATCCTCTGCCCTGAGAGG | 38 |
| HBB gRNA name | | | | |
| HBB 37.1 | GGGTTGGCCAATCTACTCCC | 39 | GGTTGGCCAATCTACTCCCAGG | 40 |
| HBB 49.2 | GGGTTGGCCAATCTACTCCC | 41 | GGGTTGGCCAATCTACTCCCAGG | 42 |
| HBB 53.1 | GGAGTAGATTGGCCAACCCT | 43 | GGAGTAGATTGGCCAACCCTAGG | 44 |
| HBB 54.1 | GATTGGCCAACCCTAGGGTG | 45 | GATTGGCCAACCCTAGGGTGTGG | 46 |
| HBB 77.1 | GAGTAGATTGGCCAACCCTA | 47 | GAGTAGATTGGCCAACCCTAGGG | 48 |
| HBB INT 1 36.2 | TGGTATCAAGGTTACAAGAC | 49 | TGGTATCAAGGTTACAAGACAGG | 50 |
| HBB INT1 36.2 REV | TCCACATGCCCAGTTTCTAT | 51 | TCCACATGCCCAGTTTCTATTGG | 52 |
| HBB INT1 47.1 | TTAAGGAGACCAATAGAAAC | 53 | TTAAGGAGACCAATAGAAACTGG | 54 |
| HBB INT1 48.1 | TAAGGAGACCAATAGAAACT | 55 | TAAGGAGACCAATAGAAACTGGG | 56 |
| HBB INT2 340.1 | CTGCCTAGTACATTACTATT | 57 | CTGCCTAGTACATTACTATTTGG | 58 |
| HBB INT2 797.1 | ATTAGCAAAAGGGCCTAGCT | 59 | ATTAGCAAAAGGGCCTAGCTTGG | 60 |
| HBB INT2 20.1 | GTTAAGTTCATGTCATAGGA | 61 | GTTAAGTTCATGTCATAGGAAGG | 62 |
| HBB INT2 39.2 | GACGAATGATTGCATCAGTG | 63 | GACGAATGATTGCATCAGTGTGG | 64 |
| HBB KO | CTTGCCCCACAGGGCAGTAA | 65 | CTTGCCCCACAGGGCAGTAACGG | 66 |
| HBB AAVS1 | GTCCCCTCCACCCCACAGTG | 67 | GTCCCCTCCACCCCACAGTGGGG | 68 |

The invention claimed is:

1. A genetically modified hematopoietic stem cell comprising, in at least one globin gene comprised in the genome thereof, at least one transgene encoding a therapeutic protein or a therapeutic ribonucleic acid, the transgene being placed under control of the endogenous promoter of the at least one globin gene,
wherein the at least one transgene encoding a therapeutic protein or a therapeutic ribonucleic acid is comprised in the 5' region, in the 3' untranslated region (3' UTR) and/or in an intron of the at least one globin gene,
wherein the at least one globin gene is selected from the group consisting of the alpha 1 globin gene and the alpha 2 globin gene.

2. The genetically modified hematopoietic stem cell according to claim 1, wherein the at least one transgene encoding a therapeutic protein or a therapeutic ribonucleic acid is comprised in the 5' region and/or in the second intron (IVS2) of the at least one globin gene.

3. The genetically modified hematopoietic stem cell according to claim 1, wherein the at least one transgene encoding a therapeutic protein or a therapeutic ribonucleic acid is comprised in the 5' untranslated region (5'UTR) and/or in the proximal promoter and/or in the second intron (IVS2) of the at least one globin gene.

4. The genetically modified hematopoietic stem cell according to claim 1, wherein
the at least one globin gene is the alpha 1 globin gene and/or the alpha 2 globin gene;
and the at least one transgene encoding a therapeutic protein or a therapeutic ribonucleic acid is comprised in the 5' untranslated region (5'UTR) or in an intron, of the at least one globin gene.

5. The genetically modified hematopoietic stem cell according to claim 1, wherein the encoded therapeutic protein is selected from the group consisting of cytokines; hormones; chemokines; antibodies; anti-angiogenic factors; enzymes for replacement therapy; insulin; G-CSF; GM-CSF; hPG-CSF; M-CSF; blood clotting factors; transmembrane proteins; lysosomal enzymes; any protein that can be engineered to be secreted and eventually taken up by non-modified cells, and combinations thereof.

6. A blood cell originating from a genetically modified hematopoietic stem cell according to claim 1.

7. A pharmaceutical composition comprising at least one genetically modified hematopoietic stem cell according to claim 1 and/or at least one blood cell originating from the at least one genetically modified hematopoietic stem cell, and a pharmaceutically acceptable medium.

8. A method for the ex vivo or in vitro preparation, of the genetically modified hematopoietic stem cell according to claim 1, comprising the steps of:
(i) providing to a hematopoietic stem cell a site-directed genetic engineering system by:
   (a) providing to the hematopoietic stem cell (1) at least one guide nucleic acid binding to a selected target site or (2) a guide peptide-containing endonuclease binding to a selected target site, the selected target site being located in an endogenous globin-encoding gene comprised in the genome of the hematopoietic stem cell, the endogenous globin-encoding gene being selected from the group consisting of the alpha 1 globin gene and the alpha 2 globin gene;
   (b) after the at least one guide nucleic acid has been provided at step a), further providing to the hematopoietic stem cell at least one endonuclease devoid of target site specificity; and
   (c) further providing to the hematopoietic stem cell a transgene that encodes at least one therapeutic protein or at least one therapeutic ribonucleic acid; and
(ii) culturing the hematopoietic stem cell obtained at step (i) such that the transgene is introduced at the said selected target site in the genome of the hematopoietic stem cell.

9. The method according to claim 8, wherein the method further comprises the steps of:
(i) providing to the hematopoietic stem cell a site-directed genetic engineering system by:
(a) providing to the hematopoietic stem cell at least one guide nucleic acid binding to a selected target site, the target site being located in the endogenous globin-encoding gene comprised in the genome of the hematopoietic stem cell;
(b) further providing to the hematopoietic stem cell at least one endonuclease devoid of target site specificity; and
(c) further providing to the hematopoietic stem cell a transgene that encodes at least one therapeutic protein or at least one therapeutic ribonucleic acid; and
(ii) culturing the hematopoietic stem cell obtained at the end of step (i) such that the transgene is introduced at the selected target site in the genome of the hematopoietic stem cell.

10. The method according to claim 8, wherein the at least one endonuclease devoid of target site specificity is a Clustered regularly interspaced short palindromic repeats (CRISPR) associated nuclease.

11. The method according to claim 8, wherein the at least one guide nucleic acid is a guide RNA which recognizes a target site in the 5' region and/or in an intron and/or in the proximal promoter and/or in an intron of the at least one globin gene comprised in the genome of the hematopoietic stem cell.

12. A method for the treatment of
a disease selected from the group consisting of autoimmune diseases, viral infections and tumors; and/or
a disease caused by the lack of a protein or by the presence of an aberrant non-functional protein in an individual in need thereof, comprising administering to the individual a therapeutically effective amount of the genetically modified hematopoietic stem cell according to claim 1, a blood cell originating from the genetically modified hematopoietic stem cell, or a pharmaceutical composition comprising the genetically modified hematopoietic stem cell or the blood cell.

13. A method for inducing immune tolerance in an individual in need thereof, comprising administering to the individual a hematopoietic stem cell according to claim 1, a blood cell originating from the hematopoietic stem cell, or a pharmaceutical composition comprising the genetically modified hematopoietic stem cell or the blood cell.

* * * * *